(12) United States Patent
Stevens et al.

(10) Patent No.: US 6,858,633 B1
(45) Date of Patent: Feb. 22, 2005

(54) SUBSTITUTED 2-ARYLBENZAZOLE COMPOUNDS AND THEIR USE AS ANTITUMOUR AGENTS

(75) Inventors: Malcolm F. G. Stevens, Leicestershire (GB); Andrew D. Westwell, Nottingham (GB); Mei-Sze Chua, Singapore (SG); Tracey D. Poole, Chesterfield (GB); Ian P. Hutchinson, Nottingham (GB)

(73) Assignee: Cancer Research Technology Limited, London (GB)

(*) Notice: Subject to any disclaimer, the term of this patent is extended or adjusted under 35 U.S.C. 154(b) by 142 days.

(21) Appl. No.: 10/069,018

(22) PCT Filed: Aug. 21, 2000

(86) PCT No.: PCT/GB00/03210

§ 371 (c)(1),
(2), (4) Date: Jul. 29, 2002

(87) PCT Pub. No.: WO01/14354

PCT Pub. Date: Mar. 1, 2001

(30) Foreign Application Priority Data

Aug. 20, 1999 (GB) .............................................. 9819673

(51) Int. Cl.⁷ .................... A61K 31/421; A61K 31/426; C07D 263/57; C07D 277/66; C07D 498/00
(52) U.S. Cl. ....................... 514/367; 514/375; 548/179; 548/217
(58) Field of Search ............................... 548/179, 217; 514/367, 375

(56) References Cited

U.S. PATENT DOCUMENTS 3,257,204 A 6/1966 Sus et al.
3,401,048 A 9/1968 Okubo et al.

FOREIGN PATENT DOCUMENTS

| DE | 2333378 | 1/1975 |
| JP | 11060573 A | 3/1999 |
| WO | WO 95/06469 | 3/1995 |
| WO | WO 96/26932 | 9/1996 |

OTHER PUBLICATIONS

Hauser, Hermann, "2–Aminophenyl benzothiazoles" *Chemical Abstracts* 22:9 (May 10, 1928) 1590 (Abstract); and *Helv. Chim. ACTA* 11 (1928) 198–209 (article).

Hutchinson et al., "The regiospecific synthesis of 5– and 7–monosubstituted and 5,6–disubstituted 2–arylbenzothiazoles" *Tetrahedron Letters* 41 (2000) 425–428.

*Primary Examiner*—Taofiq Solola
(74) *Attorney, Agent, or Firm*—Pillsbury Winthrop LLP

(57) ABSTRACT

Substituted 2-phenylbenzazole compounds of formula (I) wherein X represents S or O and Q represents a direct bond, —CH2— or —CH=Ch—, exhibt selective antiproliferactive activity in respect of mammalian tumour cells. At least in preferred enbodiments the benzene ring of the benzazole nucleus has a halogen substituent, preferably flourine, and the 2-phenyl group has a 4'-amino substituent which may be conjugated with an amino acid to provide a water soluble amino acid amide prodrug or salt thereof.

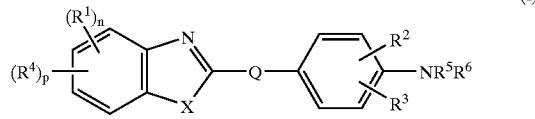

(I)

33 Claims, 2 Drawing Sheets

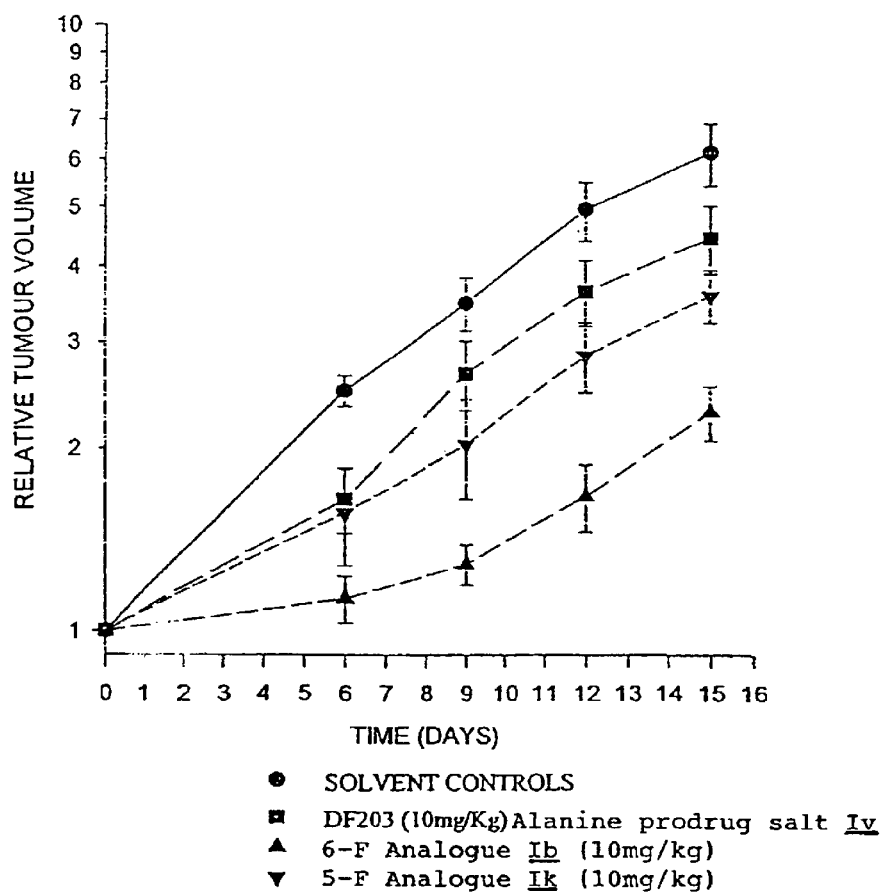

SUBSTITUTED 2-ARYLBENZAZOLE COMPOUNDS AND THEIR USE AS ANTITUMOUR AGENTS

CROSS REFERENCE TO RELATED APPLICATIONS

Figure 1:
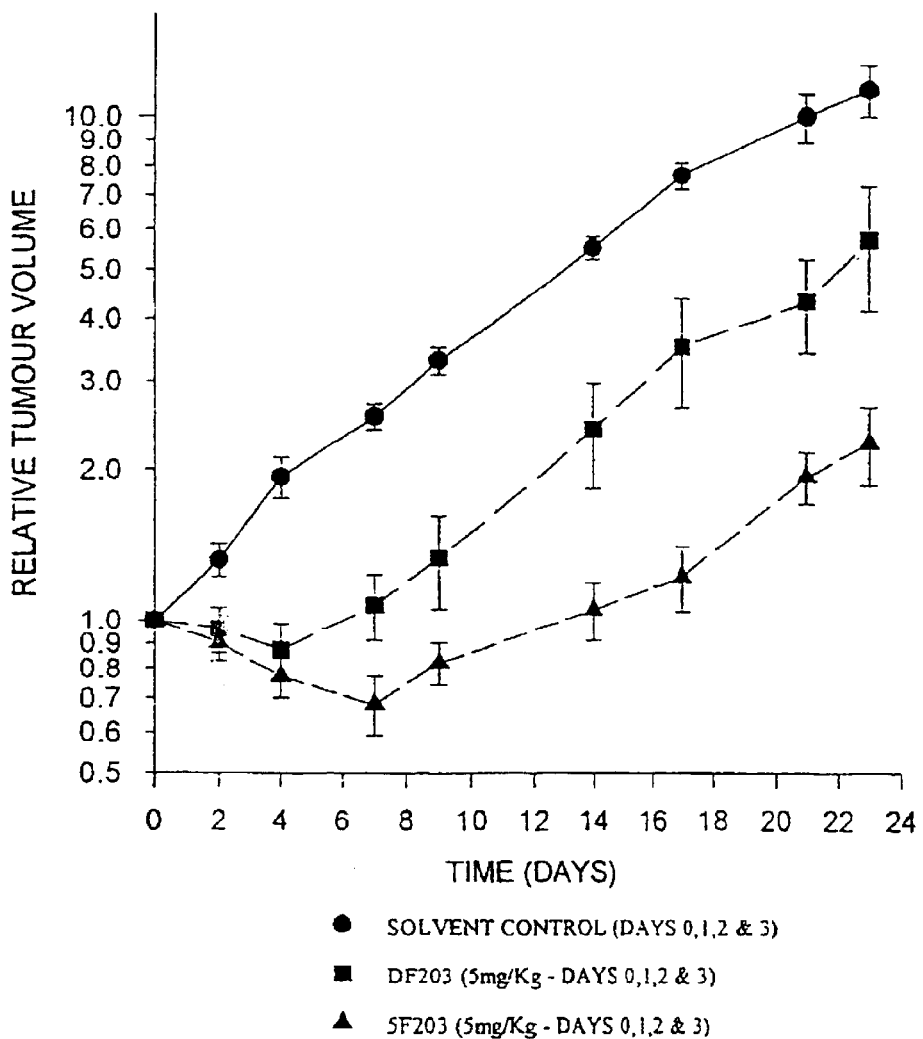

This application is a national phase application based on PCT/GB00/03210, filed Aug. 21, 2000. These application in its entirety is incorporated herein by reference.

FIELD OF THE INVENTION

The present invention relates to 2-arylbenzazole compounds. It is articularly concerned with such 2-arylbenzazole compounds which are biologically active, especially in respect of an ability selectively to inhibit proliferatiory of certain mammalian tumor cells. The invention is also concerned with compositions containing such 2-arylbenzazole compounds for use in therapy, especially antitumour therapy, and with the preparation thereof. In addition, the invention provides 2-arylbenzazole compounds which represent useful new chemical entities.

BACKGROUND AND SUMMARY OF THE INVENTION

Various 2-arylbenzazole compounds found to be active in inhibiting proliferation of certain tumor cells and exemplified by 2-(4'-aminophenyl)benzothiazole and close analogues or acid addition salts thereof are disclosed in PCT international patent publications WO 95/06469 and WO 96/26932.

For some of the benzazole compounds disclosed in WO 95/06469, for instance the compound 2-(4'-aminophenyl) benzothiazole which has been designated the reference code CJM 126, a remarkably high specific inhibitory activity has been found in respect of certain human breast cancer cell lines. In WO 96/26932 compounds such as 2-(4'-amino-3'-methylphenyl)benzothiazole (reference code DF203) for example have been disclosed that exhibit anti-proliferative activity selectively in respect of a number of different cell lines that relate to a range of various mammalian cancers other than human breast cancer.

It has now been found that by modifing the structure of the prior art compounds their antitumour activity may be improved, whilst retaining the selectivity.

As indicated, the compounds with which the present invention is concerned include 2-arylbenzazole compounds that are of particular interest as active chemotherapeutic agents for use in therapy, especially antitumor therapy, by virtue of arn ability to inhibit proliferation of certain tumor cells. Moreover, at least some of the compounds concerned are believed to be novel or new chemical entities. Furthermore, methods are provided for preparation or synthesis of the compounds, as hereinafter described. Also, in some cases the compounds are of interest as intermediates useful for the preparation of other 2-arylbenzazole compounds for use as active chemotherapeutic agents.

More particularly, according to a first aspect of the invention there is provided a compound of formula

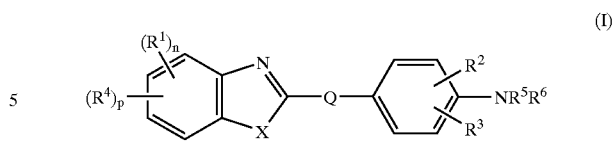

(I)

wherein
X represents S or O;
$R^1$ is selected from fluoro, iodo and trimethyltin;
$R^2$ represents hydrogen, $NO_2$, $N_3$, halogen, alkyl, a halo substituted or hydroxy substituted akli, CN or $CF_3$;
$R^3$ represents hydrogen, halogen, alkyl, or a halo substituted or hydroxy substituted alkyl;
$R^4$ represents alkyl, a halo substituted or hydroxy substituted alkyl, hydroxyl, alkoxy or aralkoxy;
$R^5$ and $R^6$ each independently represent hydrogen, an amino acid, an alkyl, or a group

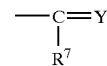

wherein Y represents O or S, and $R^7$ represents alkyl or $-CH(R^8)NH_2$ where $R^8$ represents hydrogen or an optionally substituted alkyl such as a hydroxyalkyl or amino alkyl for example;
Q represents a direct bond, $-CH_2-$ or $-CH=CH-$;
p represents zero, 1 or 2; and
n represents zero, 1, 2 or 3;
or a prodrug and/or a pharmaceutically acceptable salt thereof; subject to the following provisos:
(a) alkyl or substituted alkyl groups are linear, branched or cyclic structures but when present as linear or branched structures in the compound or as a moiety in another group such as alkoxy they are composed of less then ten carbon atoms, and preferably of less than 6 carbon atoms.
(b) p represents zero or 1 when n represents 3;
(c) when n represents zero, $R^5$ or $R^6$ represents $-C(Y)-CH(R^8)NH_2$;
(d) where a group is optionally substituted, unless otherwise specified the or each substituent is selected from halogen, OH, SH, $NH_2$, COOH and $CONH_2$;

In this specification the following definitions apply in respect of certain terms used herein:
"Aryl" dienotes a carbocyclic group or structure having at least one aromatic ring (e.g. phenyl) that in some cases may form part of a multiple condensed ring structure;
"Aralkyi" denotes a lower alkyl group, i.e. a cyclic, branched or straight chain alkyl group of one to six carbon atoms, in which there is an aryl substituent;
"Optionally substituted aryl" or "optionally substituted aralkyr" denotes aryl or aralkyl groups optionally substituted with one or more functional groups; and
"halo" denotes a fluorine, chlorine, bromine or iodine atom.

Also, the term prodrug is used in the present specification to denote modified forms or derivatives of a pharmacologically active compound which biodegrade in vivo and become converted into said active compound after administration, especially oral or intravenous administration, in the course of therapeutic treatment of a manunal. Such prodrugs are commonly chosen because of an enhanced solubility in aqueous media which helps to overcome formulation problems, and also in some case to give a relatively slow or controlled release of the active agent.

According to a second aspect the invention provides 2-arylbenzazole compounds as defined above for use in therapy. In this case, however, when n represents 1, 2 or 3, $R^1$ will usually be fluorine or iodine. The invention also provides pharmaceutical compositions comprising or containing such compounds in a form ready for administration to a mammal in need of treatment therewith.

In preferred embodiments $R^1$ will commonly represent F, preferably but not necessanfly in the 5-position. n preferably represents 1 or 2. Also, when one of $R^5$ and $R^6$ represents —C(Y)—CH($R^8$)NH$_2$, the other preferably represents hydrogen.

Fluorine substituted compounds of the invention may incorporate the isotope $^{18}$F. Such $^{18}$F-substituted compounds provide a further aspect of the invention and are of use for imaging purposes, for example as positron emitting tracers for use in positron emission tomography (PET). By administering a small amount of such $^{18}$F-substituted compounds followed by carrying out positron emission tomography in accordance with known techniques, preliminary tests may be carried out to assess the effectiveness of such compounds against a particular tumour in a patient under investigation, or to diagnose the presence of a suspected tumour using an $^{18}$F containing compound of known antitumour efficacy.

One particular $^{18}$F labelled compound useful as a tracer for positron emission tomography in tumour diagnostic studies is 5- or 6- $^{18}$Fluoro-2-(4'-amino-3'-methylphenyl) benzothiazole and amino acid conjugated prodrug forms and/or salts thereof. This may be conveniently prepared from the corresponding 5- or 6-iodo substituted compound as hereinafter described.

Preferred compounds of formula (I) wherein p represents 1 include compounds in which $R^4$ represents alkyl, alkoxy or benzyloxy. Alkyl, however, may be substituted by halogen or by hydroxy. It is also usually preferred that X represents sulphur.

Preferred compounds of formula (I) may also be further characterised by at least one of the following features:

(a) at least some alkyl groups when present as such or as a moiety in other groups such as alkoxy are methyl or ethyl;

(b) where a substituent represents or incorporates halogen, such halogen is selected from fluorine, iodine, bromine and chlorine.

A suitable prodrug of a compound of formula (I) is an amino acid amide which may be formed by conjugating the compound with the amino acid in question, e.g. alanine, lysine or sermne. Thus $R^5$ or $R^6$ optionally represents —C(O)—CH($R^8$)NH$_2$ or a salt thereof. Examples of suitable substituents for $R^8$ to represent include hydrogen, —CH$_3$, —(CH$_2$)$_4$NH$_2$ or —CH$_2$OH. The stereochemistry of the $R^5$ or $R^6$ substituent is either D or L or it is a racemic mixture. The L-stereoisomer is generally preferred.

It has been found that at least for compounds of formula (I) wherein $R^5$ and $R^6$ both represent hydrogen, i.e. wherein the phenyl group has a 4'-NH$_2$ substituent, a very effective degree of anti-proliferative activity against various mammalian tumor cells may arise when $R^2$ represents a halogen atom, or represents a $C_1$-$C_5$ lower alkyl group (preferably Me or Et), in the 3'position of the phenyl group. For example, the particular combinations of 4'-NH$_2$ and 3'-F, 4'-NH$_2$ and 3'-Cl, 4'-NH$_2$ and 3'-Br, 4'-NH$_2$ and 3'-I, 4'-NH$_2$ and 3'-Me, and 4'-NH$_2$ and 3'-Et in the phenyl group of the 2-aryl component have been found to yield compounds with potent anti-proliferative properties against at least some selected tumor cells. The 3' position substituent may alternatively be substituted by a cyano group, giving a further combination 4'-NH$_2$ and 3'-CN.

Compounds of formula (I) wherein $R^2$ is a 3'-substitueni in the phenyl group, and which are of particular interest, include those compounds where p represents zero, $R^5$ and $R^6$ both represent hydrogen, and the combination of substituents $R^3$, X and $R^2$ is selected from one of the following combinations:

| $R^3$ | X | $R^2$ |
|---|---|---|
| H | S | 3'-Me |
| H | S | 3'-Et |
| H | O | 3'-I |
| H | S | 3'-Br |
| H | S | 3'-Cl |
| H | S | 3'-CN |
| 5'-Br | S | 3'-Br |
| 5'-Cl | S | 3'-Cl |
| 5'-Me | S | 3'-Cl |
| H | S | 3'-F |

Another series of benzazole compounds which provide some very promising anti-proliferative agents for use in antitumor therapy are compounds of formula (I) wherein $R^1$ is fluorine or iodine and the substituent NR$^5$R$^6$ is a group

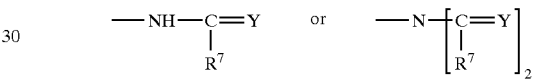

wherein, as hereinbefore specified, Y represents O or S and $R^7$ represents the group —CH($R^8$)NH$_2$ where $R^8$ is as previously defined.

Particular preferred compounds of formula (I) are those wherein p represents zero, X represents S, wherein $R^3$, $R^5$ and $R^6$ each represent H, wherein Q represents a direct bond, and wherein n, $R^1$ and $R^2$ represent one of the following combinations:

| n | $R^1$ | $R^2$ | Compound of formula |
|---|---|---|---|
| 1 | 4-F | 3-CH$_3$ | (Ia) |
| 1 | 6-F | 3-CH$_3$ | (Ib) |
| 1 | 4-F | H | (Ic) |
| 1 | 6-F | H | (Id) |
| 2 | 4,5-diF | 3-CH$_3$ | (Ie) |
| 2 | 4,6-diF | 3-CH$_3$ | (If) |
| 2 | 5,7-diF | 3-CH$_3$ | (Ig) |
| 1 | 7-F | 3-CH$_3$ | (Ih) |
| 2 | 5,6-diF | 3-CH$_3$ | (Ii) |
| 2 | 6,7-diF | 3-CH$_3$ | (Ij) |
| 1 | 5-F | 3-CH$_3$ | (Ik) |
| 1 | 5-F | H | (Il) |
| 1 | 4-F | 3-I | (Im) |
| 1 | 5-F | 3-I | (In) |
| 1 | 6-F | 3-I | (Io) |
| 1 | 4-F | 3-Cl | (Ip) |
| 1 | 5-F | 3-Cl | (Iq) |
| I | 6-F | 3-Cl | (Ir) |
| 1 | 4-F | 3-Br | (Is) |
| 1 | 5-F | 3-Br | (It) |
| 1 | 6-F | 3-Br | (Iu) |

A further particularly preferred compound is a compound of formula (I) wherein p represents zero, X represents S, Q represents a direct bond, one of $R^5$ and $R^6$ represents H and the other represents —C(Y)R$^7$ wherein Y represents O and R$^7$ represents —CH(R$^8$)NH$_2$, and wherein R$^3$ represents H, and n, R$^1$, R$^2$ and R$^8$ represents one of the following combinations:

| n    | R$^1$ | R$^2$   | R$^8$          | Compound of formula |
|------|-------|---------|----------------|---------------------|
| Zero | —     | H       | —CH$_3$        | (Iv)                |
| Zero | —     | 3-CH$_3$| —CH$_3$        | (Iw)                |
| Zero | —     | 3-Cl    | —CH$_3$        | (Ix)                |
| Zero | —     | H       | —(CH$_2$)$_4$NH$_2$ | (Iy)           |
| Zero | —     | 3-CH$_3$| —(CH$_2$)$_4$NH$_2$ | (Iz)           |
| Zero | —     | 3-Cl    | —(CH$_2$)$_4$NH$_2$ | (Iaa)          |
| Zero | —     | 3-CH$_3$| —CH$_2$OH      | (Iab)               |
| 1    | 6-F   | 3-CH$_3$| —CH$_3$        | (Iac)               |
| 1    | 5-F   | 3-CH$_3$| —(CH$_2$)$_4$NH$_2$ | (Iad)          |
| 1    | 6-F   | 3-CH$_3$| —(CH$_2$)$_4$NH$_2$ | (Iae)          |
| 1    | 5-F   | 3-CH$_3$| —CH$_3$        | (Iaf)               |
| 1    | 5-F   | 3-CH$_3$| H              | (Iai)               |

It will also be understood that many of the compounds in accordance with the invention may be in the form of pharmaceutically acceptable salts, especially acid addition salts derived from an acid selected for example from the group comprising: hydrochloric, hydrobromic, sulphuric, nitric, phosphoric, maleic, salicylic, ptoluenesulphonic, tartaric, citric, lactobionic, formic, malonic, pantothenic, succinic, naphthalene-2-sulphonic, benzene-sulphonic, methanesulphonic and ethanesulphonic.

It should also be understood, however, that where reference is made in this specification to compounds of formula (I) such reference should be construed as extending not only to their pharmaceutically acceptable salts but also to other pharmaceutically acceptable bioprecursors (prodrug forms), especially amilo acid amide derivatives as hereinbefore referred to, where relevant Moreover, where any of the compounds referred to can exist in more than one enantiomeric form or contain atoms which have more than one isotope, all such enantiomeric forms or isotopic compounds, mixtures thereof, and their preparation and uses are within the scope of the invention.

The invention also comprises the use of a 2-arylbenzazole compound as hereinbefore specified for making a medicament or pharmaceutical composition, especially for selective use in antitumor therapy.

As hereinafter more particularly described, pharmaceutical compositions or preparations in accordance with the invention for selective use in antitumor therapy will generally contain or provide a therapeutically effecfive antitumour amount of the active compound, and will be formulated in accordance with any of the methods well known in the art of pharmacy for administration in any convenient manner, and may for example be presented in unit dosage form admixed with at least one other ingredient providing a compatible pharmaceutically acceptable additive, carrier, diluent or pharmaceutically inert excipient.

Biological Results
In vitro Cytotoxicities

In carrying out the following cytoloxicity assays, the method used corresponds substantially to the following example:

Cells were maintained in a continuous logarithmic culture in RMPI 1640 with L-glutamine medium, supplemented with 10% fetal calf serum, penicillin (100 IU/ml) and streptomycin (100 µg/ml). The cells were mildly trypsinized for passage and for use in assays.
On day one, 180 µl of trypsinized tumour cells (5×10$^3$ ml$^{-1}$) were placed in the wells of 96-well, flat-bottom microtiter plates. Columns 1 and 12 were filled with 300 µl medium to protect from evaporation. The plates were incubated for 24 hours at 37° C. and 5% CO$_2$ in air to allow the cells to adhere and resume exponential growth prior to the addition of drugs. The compounds being tested were dissolved in DMSO and stored as 10 mM stock solutions at 4° C., protected from light. Serial dilutions at a 10× concentration were prepared in growth medium so that the final concentration of DMSO exposed to cells did not exceed 1%.

On day two, 20µl of growth medium was added, to the wells of column 2 to act as a control. 20 µl of drug dilution was added to the other wells with the lowest concentration in column 3 and the highest concentration in column 11. The plates were incubated for 72 hours at 37° C. and 5% CO$_2$ in air. Each compound was tested in triplicate. At the time of drug addition, a plate of untreated cells was read to provide an initial optical density value for use in the calculation of the IC$_{50}$.

On day five the plates were read. 50 µl MTT (1 mg/ml$^{-1}$) was added per well and the plates incubated for a further 4 hours. The MTT is metaboliscd to form a blue formazan product. The MTT solution was aspirattd and 125 µl DMSO:glycine buffer (4:1) was added. The plates were placed on a plate shaker until the fornazan crystals had dissolved and absorbance was ready at 550 nm on a plate reader.

For each compound tested, a dose response curve was obtained and the IC$_{50}$ statue (drug concentration at 50% inhibition of cell growth) was calculated.

It has surprisingly been found that many of the compounds of formula (I) are highly potent, inhibiting 50% cell growth at <10 nM. Examples of the results of in vitro cyctotoxicity tests carried out using MCF-7 and MDA468 cell lines are presented at the end of this description in TABLE 1 which shows IC$_{50}$ values as determined by 3-day MTT assays. (n=8) for a range of compounds in relation to MCF-7 and MDA 468 cell lines.

The selectivity of antitumor effect of the fluorinated compounds of the invention has been found to be very similar to that found for the prior art compounds disclosed in WO 96/26932, with antiproliferative activity observed in the same cell lines that were growth inhibited by their respective non-fluorinated parent compounds, e.g., breast MCF-7 and MDA 468 cells. Prostate PC 3 and non-malignant breast HBL 100 cells were unresponsive to compounds of the invention.

One feature of the prior art compounds is that they show a biphasic dose-response relationship specifically in sensitive cell lines: cell kill occurs at low nanomolar concentrations of the compounds, followed by a potentially undesirable proliferative response at low micromolar concentrations (termed the "second growth phase"). However, it has surprisingly been found that the biphasic response is eliminated in some compounds of the invention, especially when R$^1$ represents 5-F or 7-F as in compounds Ik and Ib.

In addition to breast (MCF-7, TA47D), ovarian (IGROV 1, OVCAR 3), and renal (TK 10) cell lines, the compounds of the invention wherein R$^1$ is for example 5-F have been found to be active against colon (HCC 2998) cell lines in a standard 2 day sulforhodamine B assay—in contrast, these colon cell lines respond to the non-fluorinated prior art compounds only after prolonged 6 day exposures.

Among the prodrugs, 2-(4'-amino-3'-methylphenyl)-5-fluoro-benzothiazole alanine (alanyl amide hydrochloride salt—compound Iaf) shows outstanding antitumour potency, with $IC_{50}$ in MCF-7 cells>5 fold lower than that of other anido prodrugs. None of these prodrugs elicits the biphasic dose-response.

NCI mean graphs of the amino acid salts are similar to those of their respective parent compound, with selective antitumour activity against certain ovarian (OVCAR-5), renal (TK-10) and breast (MCF-7, T-47D) cell lines.

In vivo Xenograft Studies

The compounds of formula (Ib) and (Ik) were evaluated for in vivo antitumor property in ER positive MCF-7 and ER negative MT-1 human breast tumor xenografts implanted in nude mice using the experimental details described at pages 11 and 12 of WO 96/26932. Significant growth inhibition of MCF-7 xenografts was observed with both compounds given i.p., with the 5-F compound of formula (Ik) being toxic at 12.5 mg/kg. In the MT-1 xenografts, the compound of formula (Ik) was toxic at 25 mg/kg; at the lower dose of 12.5 mg/kg, the (6-F) compound of formula (Ib) produced more pronounced growth inhibition than did the same dose of the compound of formula (Ik) although both analogues caused dose-dependent tumor growth inhibition and weight loss. Blood parameters (white blood cell and platelet counts) and the level of liver transaiminases were not adversely affected by either compound.

The in vitro growth inhibitory property of the compounds of formula (Iw) and (Iz) is paralleled by significant in vivo growth retardation of human breast tumour xenografts (ER positive MCF-7 and ER negative MT-1) implanted in nude mice. At a dose of 12.5 mg/kg (given i.v.), the alanyl-prodrug of formula (Iw) caused a greater extent of growth retardation than its lysyl—counterpart of formula (Iz) against MCF-7 xenografts. Dose-dependent body weight loss was observed with the compound of formula (Iz). In the MT-1 xenografts, the compound of formula (Iw) was toxic at 25 mg/kg, while the compound of formula (Iz) was toxic at both doses of 12.5 mg/kg and 25 mg/kg; moderate tumor growth inhibition was observed in surviving mice treated with either prodrug.

In the accompanying drawings there are illustrated typical results of tumour growth inhibition in tumour xenographs following drug treatment as detailed below.

Tumour growth inhibition observed with MCF7 xenografts treated with the compound 2-(4'-amino-3'-methylphenyl)benzothiazole (designated DF203) and compound Ik (conveniently designated 5F203) is shown in FIG. 1 of the accompanying drawings. In FIG. 2 of said drawings there is shown the tumour growth inhibition observed with COLO205 xenografts treated respectively with the alanyl prodrug form of DF203 (compound Iv), the 5F analogue of DF203 (compound Ik), and with the 6F analogue of DF203 (compound Ib).

Pharmacokinetic Studies

Although amino acid amide prodrug compounds such as those of formulae (Iw), (Iz) and (Iad) in the form of their hydrochloride salts have been found to be stable in rat and other mammalian plasma in vitro, it has surprisingly been found that these prodrugs are readily removed from such plasma and reconverted to their parent compound in vivo, e.g. when given to rats intravenously (i.v.) at a typical dose of 25 mg/kg, thereby demonstrating suitability for use as prodrugs.

By way of example, TABLE 2 below shows the plasma concentrations measured following administration to mice at a dose of 70 µmol/kg of 5F203 (compound Ik) and the lysyl prodrug analogue thereof in the form of its dihydrochloride salt (compound Iad). A similar progressive increase in concentration of the parent compound 5F203 has also been observed following addition of said lysyl prodrug analogue of 5F203 (compound Iad) to a culture of MCF-7 cells.

TABLE 2

| Mean Sample Time | Geometric Mean Plasma Concentration (µM) | |
|---|---|---|
| (min) | Compound Iad | Compound Ik |
| 3.5 | 23.67 | 1.18 |
| 6.5 | 7.35 | 1.53 |
| 9.5 | 5.05 | 1.84 |
| 12.5 | 3.47 | 2.27 |
| 15.5 | 3.33 | 3.27 |
| 20.8 | 2.80 | 2.68 |
| 30.5 | 2.24 | 3.77 |
| 45.4 | 1.16 | 3.41 |
| 60.5 | 1.25 | 4.11 |
| 90.6 | 1.06 | 3.52 |
| 120.5 | 0.41 | 2.63 |
| 240.0 | 0.08 | 1.00 |
| 360.0 | bld | 0.59 |

Preparative Methods

In most cases the compounds of formula (I) of the present invention can readily be synihesised by various routes from easily available starting materials. By way of example, several such general synthetic routes, designated Route A, Route B, Route C, Route D and Route E are described below. The substituents for the starting materials and products of these synthetic routes have the meanings given above in connection with the definition of the compound of general formula (I) unless otherwise stated.

Route A

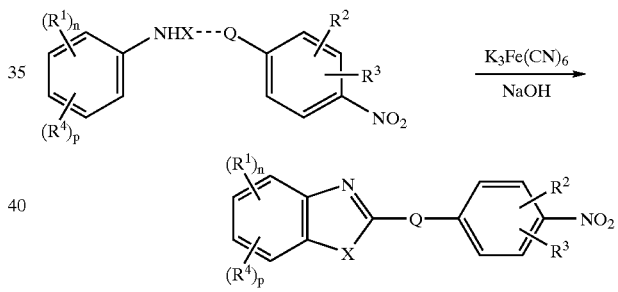

In the general method (Jacobsen cyclisation method) for Route A which is suitable when X=S, the starting material is the appropriate substituted thioberzanilide which may be prepared by reacting an optionally substituted 4-nitrobenzoyl chloride with a solution of the appropriately substituted fluoroanilinc and subsequently treating the oxybenzanilide product with Lawesson's reagent to form the thiobenzanilide. In a typical procedure, this thiobenzanilide (1 Mol. equiv.) is finely powdered and mixed with a little ethanol to form a wet paste. A 30% w/v solution of aqueous sodium hydroxide (8 Mol. equiv.) is added and diluted with water to form a suspension/solution of the thiobenzanilide in 10% w/v aqueous sodium hydroxide. Aliquots of this suspension/solution are then introduced dropwise at one minute intervals into a stirred solution of potassium ferricyanide (4 Mol. equiv.) in water at 80–90° C. The reaction mixture is heated for a further 30 minutes, then cooled. The product is collected, washed with water and crystallised. Further reduction, e.g. by heating under reflux with tin(II) chloride dihydrate in ethanol solvent, yields a compound of formula (I) wherein $R^5$ and $R^6$ each represent hydrogen. Methods well known in the art may be used to prepare further compounds of formula (I) where $R^5$ and/or $R^6$ do not represent hydrogen.

Route B

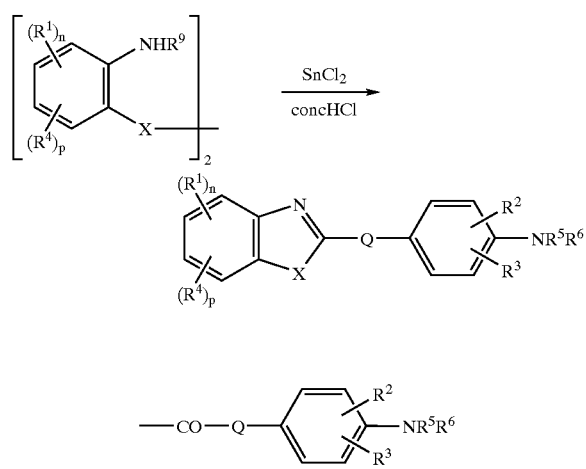

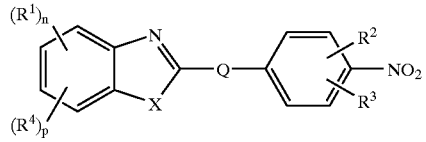

In the so-called Disulphide general method of Route B which is also suitable when X=S, typically the disulphide starting material is added together with tin(II) chloride to a solution of conc HCl, ethanol and water. The reaction mixture is heated under reflux for 15 hours, cooled to 25° C. and poured into water. Sodium hydroxide is added slowly, and the mixture stirred for 60 minutes. The precipitate is filtered from solution, and washed with water to leave a solid which is purified by column chromatography (dichloromethane) followed by recrystallisation from ethanol to give clear needles. A particular example of the use of this Disulphide Route including preparation of the disulphide starting material is hereinafter more fully described in relation to EXAMPLE 11.

Route C

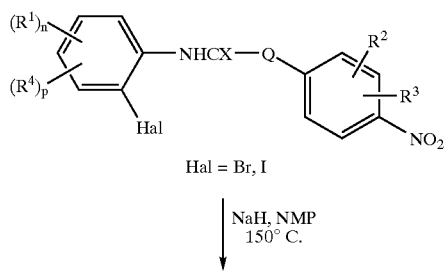

In the general method for Route C, sodium hydride (1.1 mol. equiv) is slowly added to a solution of starting material (1.0 mol. equiv) in N-methyl-2-pyrrolidinone (NMP) at room temperature with stirring. The mixture is heated at 150° C. for one hour then allowed to cool. Water (50 ml) is then added and the precipitate collected by filtration and dried in vacuo to give the solid product.

Reduction, e.g. by refluxing with tin(II) chloride in ethanol, yields a compound of formula (I) wherein $R^5$ and $R^6$ each represent hydrogen. Methods well known in the art may be used to prepare further compounds of formula (I) where $R^5$ and/or $R^6$ do not represent hydrogen.

This method is generally applicable but is especially useful for the synthesis of compounds with 7-fluoro, 5-fluoro, 5,6-difluoro and 6,7-difluoro substituents.

Route D

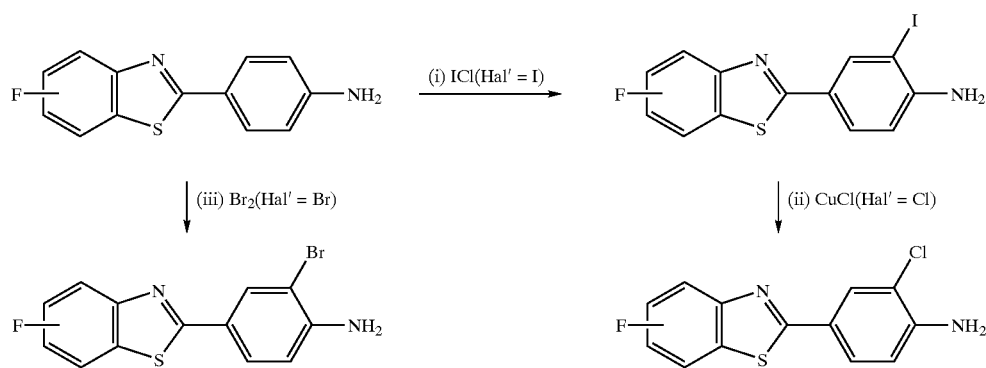

Route D is for 3'-halogenation of compounds of formula (I). The general methods for each variant are as follows:
(i) in the general method for iodination, iodine monochloride ICl is added to a solution of the starting material in acetic acid at 25° C. The resulting solution is stirred for 2 hours, then the solvent is removed under vacuum. The residue is dissolved in chloroform and washed with aqueous sodium carbonate, aqueous sodium thiosulfate and water. Evaporation of the solvent, is followed by column chromatography (chloroform) and recrystallisation from methanol giving needles.
(ii) in the general method for chlorination, a solution of the 3'-iodo compound prepared as in (i) above and copper(I) chloride in DMF is heated under reflux overnight. After cooling, the reaction mixture is poured into ethyl acetate, the precipitated solids are filtered off and the resulting solution evaporated to dryness. The product is purified by column chromatography (dichloromethane) followed by recrystallization from methanol to give a pale green solid.
(iii) in the general method for bromination, bromine is added to a solution of the original starting material in dichloromethane at 10° C. The resulting solution is stirred for 10 min, then poured into water/ice. The organic layer is removed and washed with 10% sodium thiosulfate, water and evaporated. The product is purified by column chromatography (dichloromethane) to leave a white solid.

Route E

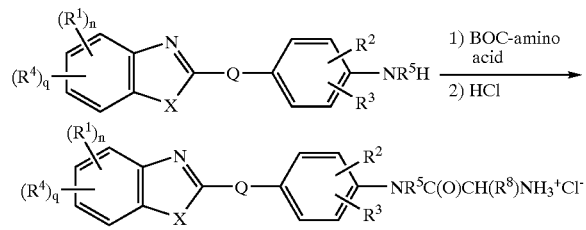

Route E is for preparing amino acid prodrug derivatives.

A compound of formula (I) wherein $R^6$ represents hydrogen (7.75 mmol) is dissolved tri dichloromethane (100 ml) and stirred at room temperature. To this solution is added 1-ethyl-3-(3'-dimethylaminopropyl)carbodiimide hydrochloride (2.3 mmol), HOBt (2.3 mmol) and the appropriate BOC protected amino acid (2.3 mmol). This procedure is repeated and the reaction is continued until a clear solution is obtained. The solvent is removed under vacuum and the resulting oil purified by column chromatography (2% methanol/dichloromethane). Recrystallisation from ethanol gives a white solid.

The BOC protected amino acid derivative thus obtained (3.5 mmol) is dissolved in dichloromethane (20 ml). Dry HCl gas is bubbled through the solution to saturate it, then the reaction mixture is stirred for a further 2 hrs at 25° C. The precipitate is filtered from solution and washed with dichloromethane (10 ml), to leave a bright yellow crystalline solid. Recrystallisation, if required, is carried out using methanol/acetolle.

Therapeutic Use

As already indicated, compounds of this invention have been found to inhibit tumor cell proliferation and to have significant selective antitumor activity. Antitumor activity may be evidenced by reduction of tumor cell number in mammals bearing cancer tumors, e.g. breast cancer tumors, and a consequent increase in survival time as compared to a control provided by animals which are untreated. Antitumor activity is further evidenced by measurable reduction in the size of solid tumors following treatment with the compounds of this invention compared to the tumors of untreated control animals.

Accordingly, as previously stated the compounds of the present invention are of particular interest for the treatment of a range of selected cancer tumors, and the invention further provides a method for the treatment of a patient suffering from certain kinds of cancer. For this purpose, a therapeutically effective non-toxic amount of a compound of formula (I) as hereinbefore defined, may be suitably administered, orally, parenterally (including subcutaneously, intramuscularly and intravenously), or topically. The administration will generally be carried out repetitively at intervals, for example once or several times a day.

The amount of the compound of formula (I) which is required in order to be effective as an antitumor agent for treating mammals will of course vary and is ultimately at the discretion of the medical or veterinary practitioner treating the mammal in each particular case. The factors to be considered by such a practitioner, e.g. a physician, include the route of administration and pharmaceutical formulation; the mammals body weight, surface area, age and general condition; and the chemical form of the compound to be administered. However, a suitable effective antitumor dose may be in the range of about 1.0 to about 75 mg/kg bodyweight, preferably in the range of about 5 to 40 mg/kg with most suitable doses being for example in the range of 10 to 30 mg/kg. In daily treatment for example, the total daily dose may be given as a single dose, multiple doses, e.g. two to six times per day, or by intravenous infusion for any selected duration. For example, in the case of a 75 kg mammal, the dose range could be about 75 to 500 mg per day, and it is expected that a typical dose would commonly be about 100 mg per day. If discrete multiple doses are indicated, treatment might typically be 50 mg of the compound of formula (I), given 4 times per day in the form of a tablet, capsule, liquid (e.g. syrup) or injection.

While it may be possible for the compounds of formula (I) to be administered alone as the raw chemical, it is preferable to present the compounds as a pharmaceutical formulation. Formulations of the present invention, for medical use, will generally comprise the compound of formula (I) together with one or more pharmaceutically acceptable carriers and, optionally, any other therapeutic ingredients. The carrier(s) must be pharmaceutically acceptable in the sense of being compatible with the other ingredients of the formulation and not deleterious to the recipient thereof.

The present invention therefore further provides a pharmaceutical formulation comprising a compound of formula (I) together with a pharmaceutically acceptable carrier thereof.

The possible formulations include those suitable for oral, rectal, topical and parenteral (including subcutaneous, intramuscular and intravenous) administration or for administration to the lung or another absorptive site such as the nasal passages.

All methods of formulation will generally include the step of bringing the compound of formula (I) into association with a carrier which constitutes one or more accessory ingredients. Usually, the formulations are prepared by uniformly and intimately bringing the compound of formula (I) into association with a liquid carrier or with a finely divided solid carrier or with both and then, if necessary, shaping the product into desired formulations.

Formulations of the present invention suitable for oral administration may be presented as discrete units such as capsules, cachets, tablets or lozenges, each containing a predetermined amount of the compound of formula (1); as a powder or granules; or a suspension in an aqueous liquid or non-aqueous liquid such as a syrup, an elixir, an emulsion or a draught. The compound of formula (I) may also be presented as a bolus, electuary or paste.

A tablet may be made by compression or moulding, optionally with one or more accessory ingredients. Compressed tablets may be prepared by compressing, in a suitable machine, the compound of, formula (I) in a freeflowing form such as a powder or granules, optionally mixed with a binder, lubricant, inert diluent, surface active or dispersing agent. Moulded tablets may be made by moulding, in a suitable machine, a mixture of the powdered compound of formula (I) with any suitable carrier.

A syrup may be made by adding the compound of formula (I) to a concentrated, aqueous solution of a sugar, for example sucrose, to which may be added any desired accessory ingredient. Such accessory ingredient(s) may include flavourings, an agent to retard crystallisation of the sugar or an agent to increase the solubility of any other ingredient, such as a polyhydric alcohol, for example glyerol or sorbitol.

Formulations for rectal administration may be presented as a suppository with a usual carrier such as cocoa butter.

Formulations suitable for parental administration conveniently comprise a sterile aqueous preparation of the compound of formula (I) which is preferably isotonic with the blood of the recipient. An injectable formulation may be made up for example with the compound 2-(4'-amino-3'-methylphenyl)-5-fluorobenzothiazole in the form of a water-soluble lysyl amide dihydrochloride salt dissolved in saline with Tween 80™ (0.05%) or 5% dextrose in water. A typical dose range in this case for use in treating humans would be 1-100 mg/m$^2$.

In addition to the aforementioned ingredients, formulations of this invention, for example ointments, creams and the like, may include one or more accessory ingredients, for example a diluent, buffer, flavouring agent, binder, surface active agent thickener, lubricant and/or a preservative (including an antioxidant) or other pharmaceutically inert excipient.

The compounds of this invention may also be made up for administration in liposomal formulations which can be prepared by methods well-known in the art.

Thus, as already indicated, the invention also comprises use of a compound of formula (I) as herein defined for the manufacture of a medical preparation, especially for use in the treatment of cancer.

EXAMPLES

The preparation of a number of particular compounds which are considered to be of especial interest for use as active therapeutic substances to inhibit proliferation of at least certain cancer cells and which provide examples of preferred embodiments of the invention (or examples of reference compounds for comparison purposes) will now be described in more detail, together with some general procedures for specific types of reactions. Some of the compounds described can also be useful as intermediates for the preparation of compounds of other embodiments. The compound or formula reference codes used elsewhere in this description are also quoted where applicable. It should be understood, however, that these specific examples are not intendedto be construed in any way as limiting the scope of the invention.

Example 1

4-Fluoro-2-4'-amino-3'-methylphenyl)benzothiazole (Ia)

3-Methyl4-nitrobenzoyl chloride (0.2 mol) was added slowly to a solution of 2-fluoroaniline (0.2 mol) in pyridine (100 ml). The resulting solution was heated under reflux for 60 min, then poured into water (300 ml). The precipitate was filtered from solution, washed with water (100 ml), followed by methanol to afford a white solid.

Lawesson's reagent (0.07 mol) was added to a solution of the benzanilide obtained (0.1 mol) in HMPA (50 ml). The resulting solution was heated at 100° C. for 15 hr, then poured into water (300 ml). The product was extracted into diethyl ether (3×300 ml) and washed with water (3×200 ml). Evaporation of the solvent followed by recrystallization from methanol gave a bright orange solid.

A solution of the fluoro substituted thiobenzanilide thus obtained (0.2 mol) in aqueous sodium hydroxide (1.8 mol in 50 ml water) containing ethanol (5 ml) was added dropwise to a solution of potassium ferricyanide (0.8 mol) in water (20 ml) at 90° C. over a period of 60 min. The resulting solution was stirred at 90° C. for a further 2 hr, then cooled in ice. The precipitate was filtered from solution and washed with water (100 ml). The product: was purified by column chromatography (30% hexane/chloroform) to leave a bright yellow solid.

The product of the previous step (0.03 mol) and tin(II) .chloride dihydrate (0.15 mol) were suspended in ethanol (150 ml) and heated under reflux for 2 hrs. The solvent was removed under vacuum and the resulting oil taken up in ethyl acetate (700 ml). The organic layer was washed with 2 M sodium hydroxide (2 ×200 ml), water (100 ml) and salt brine (30 ml). Removal of the solvent under vacuum followed by recrystallization from methanol gave the title compound as a pale yellow solid.

mp 203–205° C.; IR 3491, 3369 (NH$_2$), 1624 (C=N) cm$^{-1}$; $^1$H NMR (DMSO-d6) δ 7.86 (1H, dd, J 1.5, 8.5 Hz, H-7), 7.71 (1H, d, J2 Hz, H-2'), 7.66 (1H, dd, J 2, 8.25 Hz H-6'), 7.37–7.30 (2H, m, H-5, H-6), 6.73 (1H, d, J 8.25, H-5'), 5.78 (2H, brs, NH$_2$), 2.17 (3H, s, CH$_3$); MS (CI) m/z 259.5 (M+1); Anal (C$_{14}$H$_{11}$N$_2$SF) C, H, N.

EXAMPLE 2

6-Fluoro-2-(4'-amino-3'-methylphenyl)benzothiazole (Ib)

The method of Example 1 was carried out using 4-fluoroaniline instead of 2-fluoroaniline. The title compound was obtained as a pale yellow solid.

mp 203–205° C.; IR 3467, 3306 (NH$_2$), 1604 (C=N) cm$^{-1}$.

Example 3

4-Fluoro2-(4-aminophenyl)benzothiazole (Ic)

The method of Example 1 was carried out using 4-nitrobenzoyl chloride instead of 3-methyl-4-nitrobenzoyl chloride. The title compound was obtained as a pale yellow solid.

mp 219–221° C.; IR 3456, 3350 (NH$_2$), 1604 (C=N) cm$^{-1}$.

Example 4

6-Fluoro2-(4'-aminophenyl)benzothiazole (Id)

The method of Example 1 was carried out using 4-nitrobenzoyl chloride instead of 3-methyl-4-nitrobenzoyl chloride and 4-fluoroaniline instead of 2-fluoroaniline. The title compound was obtained as a pale yellow solid.

mp 152–155° C.; IR 3333, 3219 (N$_2$), 1604 (C=N) cm$^{-1}$.

Example 5

4,5-Difluoro-2-(4'-amino-3'-methylphenyl)benzothiazole (Ie)

The method of Example 1 was carried out 2,3-difluoroaniline instead of 2-fluoroaniline. The title compound was obtained as a pale yellow solid.

mp 204–205° C.; IR 3466, 3387 (NH$_2$), 1616 (C=N) cm$^{-1}$.

Example 6

4,6Difluoro-244'-amino-3'-methylphenyl)benzothiazole (If)

The method of Example 1 was carried out using 2,4-difluoroarifline instead of 2-fluoroaniline. The title compound was obtained as a pale yellow solid.

mp 197–199° C.; IR 3475, 3385 (NH$_2$), 1622 (C=N) cm$^{-1}$.

Example 7

5,7-Difluoro-2-(4'-amino3'-methylphenyl) benzothiazole (Ig)

The method of Example 1 was carried out using 3,5-fluoroaniline instead of 2-fluoroaniline. The title compound was obtained as a pale yellow solid.

mp 201–203° C.; IR 3483, 3323 ($NH_2$), 1616 (C=N) $cm^{-1}$.

Example 8

7-Fluoro-2-(4'-imino-3'-methylphenyl)benzothiazole (Ih)

This Example made use of the general preparative method designated Route C. 3-Methyl4-nitrobenzoyl chloride (0.2 mol) was added slowly to a solution of 2-bromo-3-fluoroaiiiline (0.2 mol) in pyridine (100 ml). The resulting solution was heated under reflux for 60 min, then poured into water (300 ml). The precipitate was filtered from solution, washed with water (100 ml), followed by methanol to afford a white solid.

Lawesson's reagent (0.07 mol) was added to a solution of the benzanilide obtained (0.1 mol) in HMPA (50 ml). The resulting solution was heated at 100° C. for 15 hr, then poured into water (300 ml). The product was extracted into diethyl ether (3×300 ml) and washed with water (3×200 ml). Evaporation of the solvent followed by recrystallization from methanol gave a bright orange solid.

Sodium hydride (0.22 mol) was slowly added to a solution of the fluoro substituted thiobenzanilide thus obtained (0.2 mol) in N-methyl-2-pyrrolidinone (2 mol) at room temperature with stirring. The mixture was heated at 150° C. for one hour then allowed to cool. Water (50 ml) was then added and the precipitate collected by filtration and dried in vacuo to give the product as a white solid.

The product of the previous step (0.03 mol) and tin(II) chloride dihydrate (0.15 mol) were suspended in ethanol (150 ml) and heated under reflux for 2 hours. The solvent was removed under vacuum and the resulting oil taken up in ethyl acetate (700 ml). The organic layer was washed with 2 M sodium hydroxide. (2×200 ml), water (100 ml) and salt brine (30 ml). Removal of the solvent under vacuum followed by recrystallization from methanol gave the title compound as a pale yellow solid.

mp 175–177° C.; IR 3021, 1621 (C=N), 1470, 1215, 750 $cm^{-1}$.

Example 9

5,6-Difluoro-2-(4'-amino-3'-methylphenyl) benzothiazole (Ii)

The method of Example 8 was carried out using 2-bromo4,5-difluoroaniline instead of 2-bromo-3-fluoroaniline. The product was obtained as a pale yellow solid.

mp 226–228° C.; IR 3497, 3333, 1.632, 1466, 1454, 1406, 1314, 1142 $cm^{-1}$. Example 10

6,7-Difluoro-2-(4'-amino3'-methylphenyl) benzothiazole (Ij)

The method of Example 8 is carried out using 2-bromo-5,6difluoroaniline instead of 2-bromo-3-fluoroaniline.

Example 11

5-Fluoro-2-(4'-amino-3'-methylphenyl)benzothiazole (Ik)

"Disulphide Route"

2-Amino-5-fluorobenzothiazole (5 g, 0.03 mol) was added to a solution of potassium hydroxide (25 g) in water (50 ml). The resulting mixture was heated under reflux for 5 hr, after which complete solution had occurred. After cooling, the reaction mixture was made acidic (pH 6) by the addition of acetic acid. A further portion of water (50 ml) was added and the resulting mixture stirred overnight. The solid precipitate was filtered from solution and recrystallized from ethanol/water to give bis-2-amino-5-fluorophenyl) disulphide as a pale yellow solid.

3-Methyl4-nitrobenzoyl chloride (1.45 g, 7.3 mmol) was added to a solution of bis-(2-amino-5-fluorophenyl) disulfide (1 g, 3.65 mmol) in pyridine (10 ml). The resulting mixture was heated under reflux for 30 min. then poured into water (50 ml). The precipitate was filtered from solution, and washed with water (50 ml) to leave bis-[2-(3'-methyl4'-nitrobenzanilide)-5-fluorophenyl] disulfide as a pale yellow solid.

Then, as described in relation to the preparative method designated Route B, to a solution of conc HCl (10 ml), ethanol (20 ml) and water (2 ml) was added the bis-[2-(3'-methyl-4'-nitrobenzanifide)-5-fluorophenyl] disulfide (1 g, 1.6 mmol) together with tin(II) chloride (1.86 g, 9.8 mmol). The reaction mixture was heated under reflux for 15 hr, cooled to 25° C. and poured into water (75 ml). Sodium hydroxide (2 g) was added slowly, and the mixture stirred for 60 min. The precipitate was filtered from solution, and washed with water (10 ml) to leave a yellow solid which was purified by column chromatography (dichloromethane) followed by recrystallization from ethanol to give colorless needles.

mp 195–196° C.; IR 3433, 3302 ($NH_2$), 1622 (C=N) $cm^{-1}$.

Example 12

5-Fluoro-2-(4'-aminophenyl)benzothiazole (Il)

4-Nitrobenzoyl chloride (1.35 g, 7.3 mmol) was added to a solution of bis-(2-amino-5-fluorophenyl) disulfide prepared as described in Example 11 (1 g, 3.65 mmol) in pyridine (10 ml). The resulting mixture was heated under reflux for 30 min, then poured into water (50 ml). The precipitate was filtered from solution, and washed with water (50 ml) to leave bis-[2-(4'-nitrobenzanilide)-5-fluorophenyl] disulfide as a pale yellow solid.

To a solution of conc HCl (10 ml), ethanol (10 ml) and water (2 ml) was added bis-[2-(4'-nitrobenzanilide)-5-fluorophenyl] disulfide (1 g, 1.7 mmol) and tin(II) chloride (1 g, 5.2 mmol). The reaction mixture was heated under reflux for 15 hr, cooled to 250° C. and poured into water (75 ml). Sodium hydroxide (2 g) was added slowly, and the mixture stirred for 60 min. The precipitate was filtered from solution, find washed with water (10 ml) to leave a yellow solid which was purified by column chromatography (dichloromethane) followed by recrystallization from ethanol to give colorless needles.

mp 153–155° C.; IR 3460, 3290 ($NH_2$), 1637 (C=N) $cm^{-1}$.

Example 13

4-Fluoro-2-(4'-amino-3'-iodophenyl)benzothiazole (Im)

A solution of the 4-fluoro-2-(4'-aminophenyl) benzothiazole prepared as described in Example 3 (4.5 mmol) in acetic acid (20 ml) was added dropwise to a solution of iodine monochloride (5.8 mmol) in acetic acid (20 ml) at 25° C. The resulting solution was stirred for 2 hr, then the solvent was removed under vacuum. The residue was dissolved in chloroform (100 ml) and washed with aqueous sodium carbonate (50 ml), aqueous sodium thiosulfate (50 ml) and water (50 ml). Evaporation of the solvent, followed by column chromatography (chloroform) and recrystallization from methanol gave pale cream needles.

mp 210–211° C.; IR 3474, 3377 ($NH_2$), 1610 (C=N) $cm^{-1}$.

Example 14

5-Fluoro-2-(4'-amino-3'-iodophenyl)benzothiazole
(In)

The method of Example 13 was carried out using the 5-fluoro-2-(4'-aminophenyl)benzothiazole prepared as described in Example 12 instead of 4-fluoro-2-(4'-aminophenyl) benzothiazole.

mp 187–188° C.; IR3447, 3317 ($NH_2$), 1612 (C=N) $cm^{-1}$.

Example 15

6-Fluoro-2-(4'-amino-3'-iodophenyl)benzothiazole
(Io)

The method of Example 13 was carried out using the 6-fluoro-2-(4'-aminophenyl)benzothiazole prepared as described in Example 4 instead of 4-fluoro-2-(4'-aminophenyl) benzothiazole.

mp 198–200° C.; IR 3445, 3290 ($NH_2$), 1620 (C=N) $cm^{-1}$.

Example 16

4-Fluoro-2-(4'-amino-3'-chlorophenyl)benzothiazole
(Ip)

A solution of the 4-fluoro substituted 2-(4'-amino-3'-iodophenyl)benzothiazole prepared as described in Example 13 (1.35 mmol) and copper(I) chloride (6.75 mmol) in DMF (5 ml) was heated under reflux overnight. After cooling, the reaction mixture was poured into ethyl acetate (100 ml), the precipitated solids were filtered off and the resulting solution evaporated to dryness. The product was purified by column chromatography (dichloromethane) followed by recrystallization from methanol to give a pale green solid.

mp 181–1830° C.; IR 3477, 3381 ($NH_2$), 1620 (C=N) $cm^{-1}$.

Example 17

5-Fluoro-2-(4'-amino-3'-chlorophenyl)benzothiazole
(Iq)

The method of Example 16 was carried out using the 5-fluoro substituted 2-4'-amino-3'-iodophenyl)benzothiazole prepared as described in Example 14 instead of 4-fluoro substituted 2-(4'-amino-3'-iodophenyl)benzothiazole.

mp 177–178° C.; IR 3481, 3369 ($NH_2$), 1631 (C-N) $cm^{-1}$.

Example 18

6-Fluoro-2-(4'-amino3'chlorophenYl)benzothiazole
(Ir)

The method of Example 16 was carried out using the 6-fluoro substituted 2-(4'-amino-3'-iodophenyl) benzothiazole prepared as described in Example 15 instead of 4-fiuoro substituted 2-(4'amino-3'-iodophenyl) benzothiazole.

mp 194–1950° C.; IR 3472, 3310 ($NH_2$), 1628 (C=N) $cm^{-1}$.

Example 19

4-Fluoro-2-(4'amino-3'-bromophenyl)benzothiazole
(Is)

Bromine (0.8 mmol) was added to a solution of the 4-fluoro-2-(4'-aminophenyl) benzothiazole prepared as described in Example 3 (0.8 mmol) in dichloromethane (20 ml) at 10° C. The resulting solution was stirred for 10 min, then poured into water/ice (10 ml). The organic layer was removed and washed with 10% sodium thiosulfate (10 ml), water (10 ml) and evaporated. The product was purified by column chromatography (dichloromethane) to leave a white solid.

mp 211–213° C.; IR 3416, 3379 ($NH_2$), 1618 (C=N) $cm^{-1}$.

Example 20

5-Fluoro-2-(4'-amino-3'-bromophenyl)benzothiazole
(It)

The method of Example 19 was carried out using the 5-fluoro-2-(4'-aminophenyl) benzothiazole prepared as described in Example 12 instead of 4-fluoro-2-(4'-aminophenyl) benzothiazole.

mp 181–183° C.; IR 3464, 3311 ($NH_2$), 1612 (C=N) $cm^{-1}$.

Example 21

6-Fluoro2-(4'-amino-3'-bromophenyl)benzothiazole
(Iu)

The method of Example 19 was carried out using the 6fluoro-2-(4'-aminophenyl) benzothiazole prepared as described in Example 4 instead of 4-fluoro-2-4'-aminophenyl) benzothiazole.

mp 209–211° C.; IR 3462, 3300 $NH_2$), 1626 (C=N) $cm^{-1}$.

Example 22

2-(4'-Aminophenyl)benzothiazole Alanyl Amide Hydrochloride Salt (Iv)

2-(4'-Aminophenyl)benzothiazole (7.75 mmol) was dissolved in dichloromethane (100 ml) and stirred at room temperature. To this solution was added 1-ethyl-3-(3'-dimethylaminopropyl)carbodiimide hydrochloride (2.3 mmol), HOBt (2.3 mmol) and Boc protected alanine (2.3 mmol). After stirring for 24 hrs a further 2.3 mmol of each reactant was added, and stirring continued for a further 24 hrs. This procedure was repeated twice more and stirring continued for a further 3 days, until a clear solution formed. The solvent was removed under vacuum and the resulting oil purified by column chromatography (2% methanol/dichloromethane). Recrystallisation from ethanol gave a white solid.

The Boc protected amino acid derivative thus obtained (3.5 mmol) was dissolved in dichloromeihane (20 ml). Dry HCl gas was bubbled through the solution to saturate it, then the reaction mixture was stirred for a further 2 hrs at 25° C.

The precipitate was filtered from solution and washed with dichloromethane (10 ml), to leave a bright yellow crystalline solid.

mp 258–259° C.; MS (AP) m/z 298 (M+1).

Example 23

2-(4'-Amino-3'-methylphenyl)benzothiazole Alanyl Amide Hydrochloride Salt (Iw)

The title compound was prepared using the method of Example 22 but with 2-(4'-arnino-3'-methylphenyl)benzothiazole instead of 2-(4'-aminophenyl)-benzothiazole.

mp 272–274° C.; MS (AP) m/z 312 (M+1).

Example 24

2-(4'-Amino-3'-chlorophenyl)benzothiazole Alanyl Amide Hydrochloride Salt

The title compound was prepared using the method of Example 22 but with 2-(4'-amino-3'-chlorophenyl)benzothiazole instead of 2-(4'-aminophenyl)-benzothiazole.

mp 240–243° C.; MS (AP) m/z 332 (M+1).

Example 25

2-(4'-Aminophenyl)benzothiazole Lysine Amide Dihydrochloride Salt (Iy)

The title compound was prepared using the method of Example 22 but with BOC protected lysine instead of BOC protected alanme.

mp 296–298° C.; MS (AP) m/z 355 (M+1).

Example 26

2-(4'-Amino-3'-methylphenyl)benzothiazole Lysyl Amide Dihydrochioride Salt (Iz)

The title compound was prepared using the method of Example 22 but with 2-(4'-amino-3'-methylphenyl)benzothiazole instead of 2-(4'-amino-phenyl)benzothiazole and BOC protected lysine instead of BOC protected alanine.

mp 290–293° C.; MS (AP) m/z 369 (M+1).

Example 27

2-(4'-Amino-3'-chlorophenyl)benzothiazole Lysyl Amide Dihydrochloride Salt (Iaa)

The title compound was prepared using the method of Example 22 but with 2-(4'-amino-3'-chlorophenyl)benzothiazole instead of 2-(4'-aminophenyl)-benzothiazole and BOC protected lysine instead of BOC protected alanine.

mp 278–279° C.; MS (AP) m/z 389 (M+1).

Example 28

2-(4'-Anino-3'-methylphenyl)benzothiazole Seryl Amide Hydrochloride Salt (Iab)

The title compound was prepared using the method of Example 22 but with 2-(4'-amino3'-methylphenyl)benzothiazole instead of 2-(4'-aminophenyl) benzothiazole and BOC protected serine instead of BOC protected alanine.

mp 265–269 0C.; MS (CI) m/z 328 (M+1).

Example 29

6-Fluoro-2-(4'-amino-3'-Methylphenyl)benzothiazole Alanyl Amide Hydrochloride Salt (Iac)

The title compound was prepared using the method of Example 22 but with 6-fluoro-2-(4'-amino-3'-methylphenyl)benzothiazole prepared as described in Example 2 instead of 2-(4'-aminophenyl) benzothiazole.

mp 282–2859° C.; MS (CI) m/z 330.3 (M+1).

Example 30

5-Fluoro-2-(4'-amino-3'-methylphenyl)benzothiazole Lysyl Amide Dihydrochloride Salt (Iad)

The title compound was prepared using the method of Example 22 but with 5-fluoro-2-(4'-amino-3'-methylphenyl)benzothiazole prepared as described in Example 11 instead of 2-(4'-aminophenyl)benzothiazole and BOC protected lysine instead of BOC protected alanine.

mp 290–294° C., MS (CI) m/z 387.4 (M+1).

Example 31

6-Fluoro-2-(4'-amino-3'-methylphenyl)benzothiazole Lysyl Amide Dihydrochloride Salt (Iae)

The title compound was prepared using the method of Example 22 but with 6-fluoro-2-4'-amino-3'-methylphenyl)benzothiazole prepared as described in Example 2 instead of 2-4'-aminophenyl)benzothiazole and BOC protected lysine instead of BOC protected alanine.

mp 298–303° C.; MS (CI) m/z 387.2 (M+1).

Example 32

5-Fluoro-2-(4'-amino-3'-metbylphenyl)benzothiazole Alanyl Amide Hydrochloride Salt (Iaf)

The title compound was prepared using the method of Example 22 but with 5-fluoro-2-(4-amino-3'-metylphenyl)benzothiazole prepared as described in Example 11 instead of 2-(4'-aminophenyl)benzothiazole.

mp 280–284° C.; MS (CI) m/z 330.3 (M+1).

Example 33

5-Fluoro-244'-amino-3'-methylphenyl)benzothiazole Glycyl Amide Hydrochloride Salt salt (Iai)

The title compound is prepared using the method of Example 22 but with 5-fluoro-2-(4'-amino-3'-methylphenyl)benzothiazole prepared as described in Example 11 instead of 2-4'-aminophenyl)benzothiazole and with BOC protected glycine instead of BOC protected alanine.

Example 34

5-Iodo-2-(4'-amino-3'-methylphenyl)benzothiazole (Iak)

This was synthesised via a Jacobson cyclisation reaction from the appropriate benzanilide following the method of Route A and was separated from the 7-iodo isomer by column chromatography (25% hexane dichloromethane) prior to reduction of the nitro group to amine.

Yield=92%; mp 200–202° C.; IR 3429, 3288 cm$^{-1}$; MS (CI) m/z 367.1 (M+1).

This compound can also be prepared from the appropriate 3-iodoaniline using the "Disuiphide Route" previously referred to.

Example 35

7-Iodo-2-(4'-amino-3'-methylphenyl)benzothiazole (Ial)

This was synthesised via Jacobson cyclisation, as above. It was separated from the 5-iodo isomer by column chromatography (25% hexane/dichloromethane) prior to reduction of the nitro group to amine.

Yield=93%; mp) 158–159° C.; IR 3477, 3306 cm$^{-1}$; MS (CI) m/z 366.9 (M+1).

Example 36

5-Fluoro-2-(4'-acetamido-3'-methylphenyl)benzothiazole (Iam)

Acetyl Chloride (0.09g, 1.55 mmol) was added to a solution of 5-fluoro2-(4'-amino-3'-methylphenyl)benzothiazole (0.2 g, 0.78 mmol) in chloroform (5 ml) containing triethylamine (86 mg, 0.85 mmol). The resulting solution was stirred for 30 min, then poured into water (20 ml). The organic layer was removed, dried ($Na_2SO_4$) and evaporated. Recrystallisation from ethanol gave a white solid.

Yield=86%; mp 219–221° C.; MS (CI) m/z 301.3 (M+1).

Example 37

5-Fluoro-2-(4'-amino-3'-cyanophenyl)benzothiazole (Ian)

5-Fluoro-2-(4'-amino-3'-iodophenyl)benzothiazole (5 g, 0.0135 mol), copper cyanide (3.65 g, 0.04 mol) and DMF (100 ml) were heated under reflux for 6 hrs, cooled and the solvent removed under vacuum. The residue was stirred in water (50 ml) for 30 mins, then the product extracted with ethyl acetate (2×100 ml). The combined extracts were dried ($Na_2SO_4$), evaporated and the residue recrystallised from ethanol to give a white solid.

Yield=88%; mp 268–270° C.; IR 3464, 3369, 2218 (CN) cm$^{-1}$; MS (CI) m/z 270.1 (M+1).

Example 38

4Fluoro-2-(4'-amnino-3'-cvanophenyl)benzothiazole (Iao)

This was synthesised from 4-fluoro-2-(4'-amino-3'-iodophenyl)benzothiazole by a method analogous to that used for 5-fluoro-2-(4'-amino-3'-cyanophenyl)benzozole.

Yield=18%; mp 225–227° C.; IR 3471, 3366, 2216 (CN), 1642 cm$^{-1}$; MS (CI) m/z 270 (M+1).

Example 39

6Fluoro-2-(4'-aino-3'-cyanophenyl)benzothiazole (Iap)

This was synthesised from 6-fluoro-2-(4'-amino-3'-iodophenyl)benzothiazole by a method analogous to that used for 5-fluoro-2-(4'-amino-3'-cyanophenyl)benzothiazole.

Yield=12%; mp 258–260° C.; IR 3412, 2216 (CN), 1642 cm$^{-1}$; MS (CI) m/z 270 (M+1).

Example 40

5-Fluoro-2-(4'-amino-3'-(hydroxymethyl)phenyl)benzothiazole (Iaq)

5-Fluoro-2-(4'-amino-3'-cyanophenyl)benzothiazole (1 g, 3.75 mmol) was dissolved in 80% sulfuric acid (50 ml) and heated at 100° C. for 2 hrs. After cooling, the reaction mixture was diluted with water (100 ml) and the pH adjusted to 7.5 using 50% sodium hydroxide. The product was extracted with ethyl acetate(3×50 ml), the extracts dried ($Na_2SO_4$) and evaporated to leave a yellow solid which was taken up in THF (20 ml) and added dropwise to a solution of $LiAlH_4$ (0.7 g, 0.019 mol) in THF (15 ml). After stirring at 25° C. for 2 hrs, water (20 ml) was added and the product extracted with ethyl acetate (3×50 ml). The organic extracts were washed with brine (10 ml), dried ($Na_2SO_4$) and evaporated. The residue was purified by column chromatography (10% ethyl acetate/dichloromethane) to leave a yellow powder.

Yield=34%; mp 242–245° C.; IR 3379, 3333, 1448 cm$^{-1}$; MS (CI) m/z 275.1 (M+1).

Example 41

5,6-Difluoro-2-(4'-amino-3'-methylphenyl)benzothiazole Alany Amide Hydrochloride Salt (Iar)

Synthesised by same method as 5-fluoro analogue (Iaf).

Yield=96%; mp 268–270°C.; MS (CI) m/z 348.0 (M+1).

Example 42

5,6-Difluoro-2-(4'-amino-3'-methylphenyl)benzothiazole Lysyl Amide Dihydrochloride (Ias)

Synthesised by same method as 5-fluoro analogue (Iad).

Yield=74%; mp 278–281° C.; MS (CI) m/z 405.0 (M+1).

Example 43

5-Trimethylstannyl-2-(4'-amino-3'-methylphenyl)benzoihiazole (Iat)

5-Iodo-2-(4'-amino-3'-methylphenyl)benzothiazole (Compound Iak) (1.4 g, 4.12 mmol) and tetralas triphenylphosphine palladium (48 mg, 0.41 mmol) were dissolved in dioxane (20 ml) and placed under nitrogen. Hexamethylditin (5 g, 0.15 mol) was added and the resulting solution heated under reflux for 4 hrs. The precipitated palladium was filtered from solution and washed with ethyl acetate (50 ml). The organic fractions were evaporated and chromatographed (chloroform) to leave a white waxy solid. Recrystallisation from ethanol gave clear needles.

Yield=85%; mp 158–160° C.; MS (CI) m/z 402.8, 403.4, 404.9, 405.5 (M+1).

Example 44

5-$^{18}$Fluoro-2-(4'-amino-3'-methylbenzothiazole)

The compound Iat of Example 44 can be used as an intermediate in the preparation of the above $^{18}$F labelled 5-fluoro compound from the corresponding 5-iodo substituted compound mentioned earlier. In this case the compound Iat is reacted at −20° C. with $(CF_3CO)_2O$ in the presence of $Na_2CO_3$ and $CH_2Cl_2$ to form the trifluoroacetyl derivative which is then converted into the title compound by reacting with $^{18}$F acetyl hypofluorite followed by acid hydrolysis. The overall scheme is depicted in the diagram below.

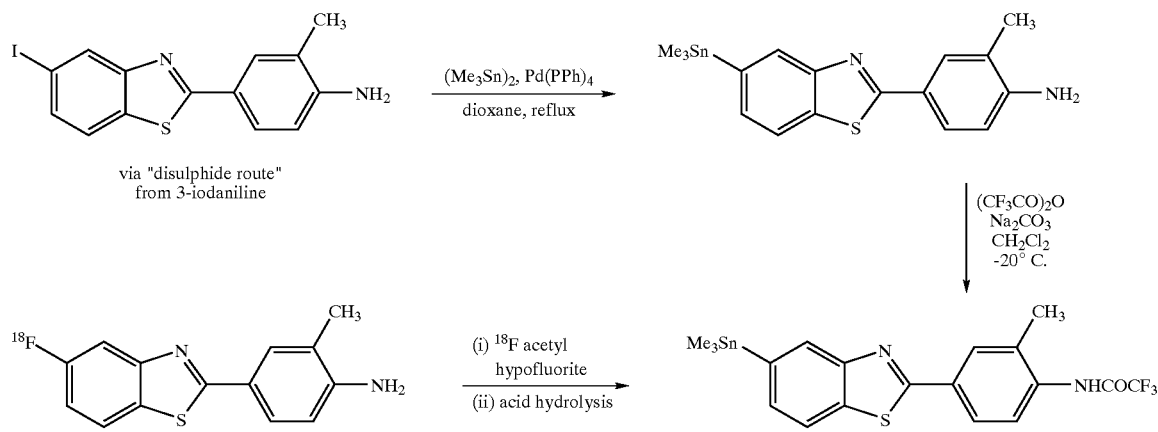

Of the compounds described above, the compound 5-fluoro-2-(4′-amino-3′-methylphenyl)benzothiazole Ik and its lysyl amino acid amide prodrug Iad, in the form for instance of its water soluble dihydrochloride salt prepared as in Example 30 from its parent compound, are of especial interest for clinical use as effective antitumour agents. The solubility of this particular prodrug Iad in water and its chemical robustness makes it very suitable for parenteral administration as an injectable formulation, sterilised by filtration, after which it becomes converted in vivo to the 5-fluoro substituted compound Ik.

As an alternative to the "disulphide" preparative method described for compound Ik in Example 11, it may also be prepared by a "Regiospecific Cyclisation" Route involving in part the general method of Route C. Both these schemes are illustrated in the diagram below, together with the scheme for converting the compound Ik into the prodrug Iad.

"Disulphide" Route

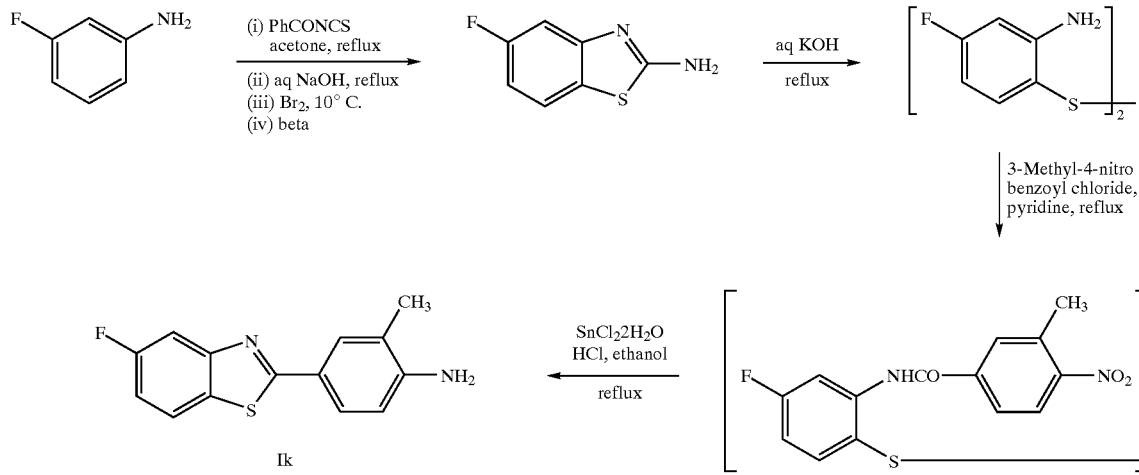

"Regiospecific Cyclization" Route

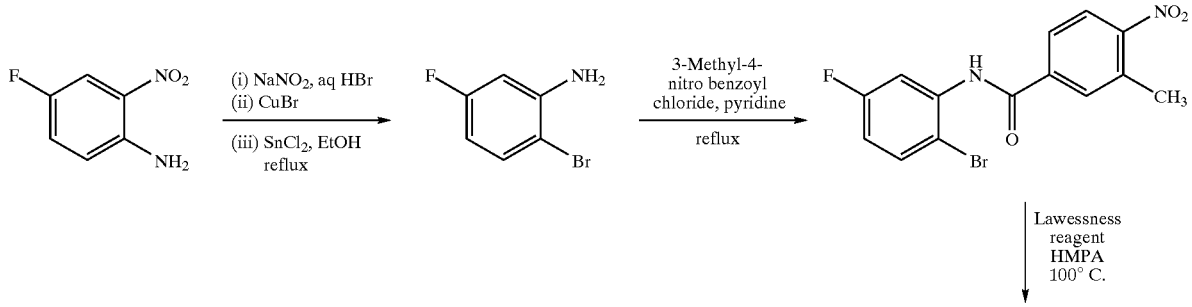

-continued

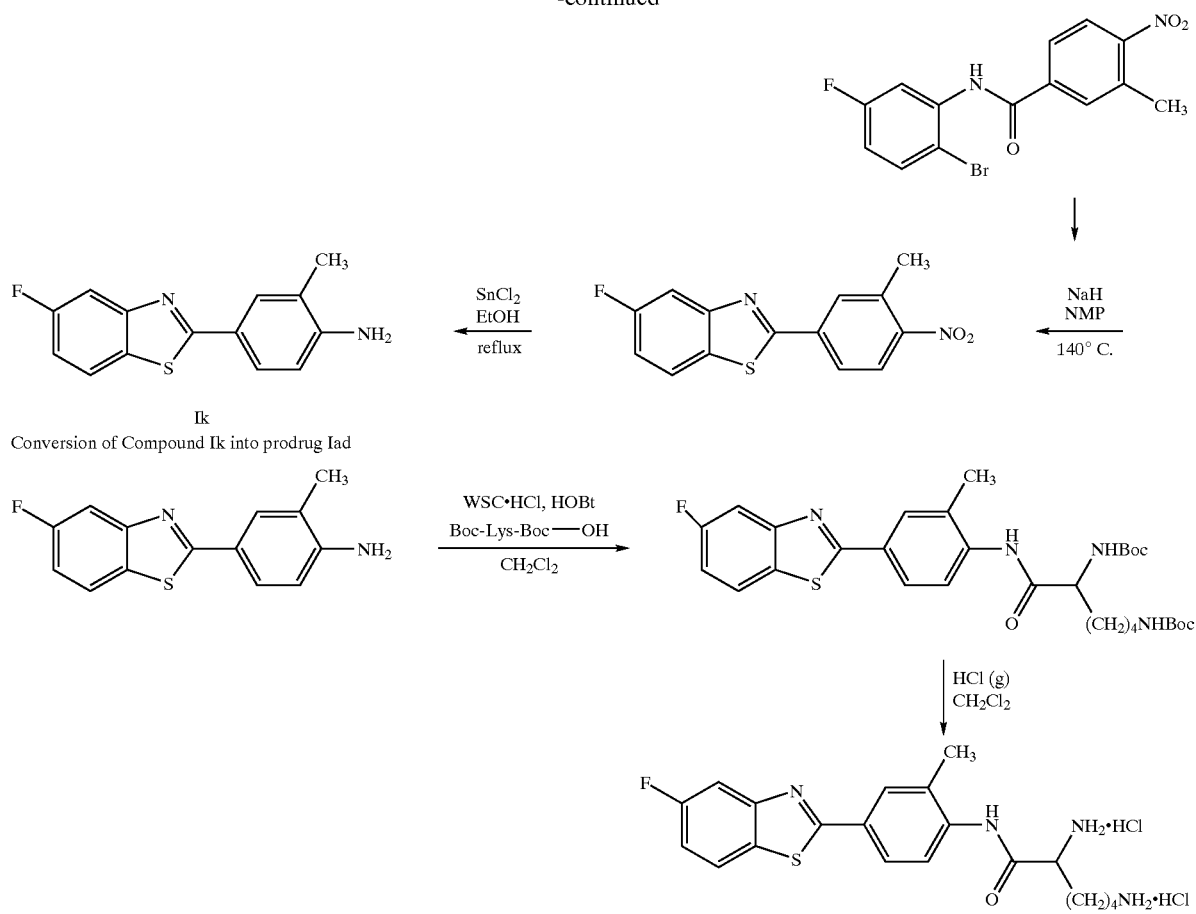

Ik
Conversion of Compound Ik into prodrug Iad

As will be seen, the invention presents a number of different aspects and it should be understood that it embraces within its scope all novel and inventive features and aspects herein disclosed, either explicitly or implicitly and either singly or in combination with one another. This includes the methods or processes for preparing or synthesising the compounds referred to. It will, however, also be understood that many detailed modifications are possible and, in particular, the scope of the invention is not to be construed as being limited solely by the illustrative example(s) or by the terms and expressions used herein merely in a descriptive or explanatory sense.

TABLE 1

In vitro activity ($IC_{50}$ concentration in nM) of various compounds of Formula (I)

(I)

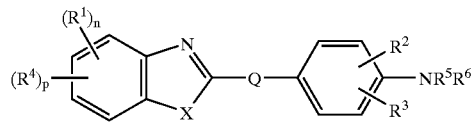

wherein
p = O, X = S, Q is a direct bond; $R^3$ = H, Y = O, $R^7$ = —CH($R^8$)$NH_3$Cl

| n | $R^1$ | $R^2$ | $R^5$ | $R^6$ | $R^8$ | $IC_{50}$ in MCF-7 | $IC_{50}$ in MDA468 | Compound of formula |
|---|---|---|---|---|---|---|---|---|
| 1 | 4-F | 3-$CH_3$ | H | H | | <0.1 | 0.13 | Ia |
| 1 | 6-F | 3-$CH_3$ | H | H | | <0.1 | 0.11 | Ib |
| 1 | 4-F | H | H | H | | 8.54 | 29.4 | Ic |
| 1 | 6-F | H | H | H | | <0.1 | 48.1 | Id |
| 2 | 4,5-diF | 3-$CH_3$ | H | H | | 0.64 | 0.67 | Ie |
| 2 | 4,6-diF | 3-$CH_3$ | H | H | | <0.1 | 5.35 | If |
| 2 | 5,7-diF | 3-$CH_3$ | H | H | | 0.9 | 4.4 | Ig |
| 1 | 7-F | 3-$CH_3$ | H | H | | 2.39 | 10.35 | Ih |
| 2 | 5,6-diF | 3-$CH_3$ | H | H | | <0.1 | 3.55 | Ii |
| 1 | 5-F | 3-$CH_3$ | H | H | | <0.1 | <0.1 | Ik |

TABLE 1-continued

In vitro activity (IC$_{50}$ concentration in nM) of various compounds of Formula (I)

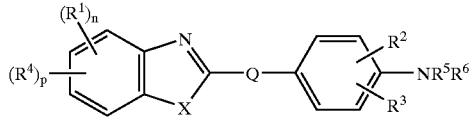

(I)

wherein
p = 0, X = S, Q is a direct bond; R$^3$ = H, Y = O, R$^7$ = —CH(R$^8$)NH$_3$Cl

| n | R$^1$ | R$^2$ | R$^5$ | R$^6$ | R$^8$ | IC$_{50}$ in MCF-7 | IC$_{50}$ in MDA468 | Compound of formula |
|---|---|---|---|---|---|---|---|---|
| 1 | 5-F | H | H | H | | <0.1 | <0.1 | Il |
| 1 | 4-F | 3-I | H | H | | 7.88 | 9.11 | Im |
| 1 | 5-F | 3-I | H | H | | <0.1 | <0.1 | In |
| 1 | 6-F | 3-I | H | H | | <0.1 | <0.1 | Io |
| 1 | 4-F | 3-Cl | H | H | | 0.95 | 1.93 | Ip |
| 1 | 5-F | 3-Cl | H | H | | 7.09 | 18.9 | Iq |
| 1 | 6-F | 3-Cl | H | H | | 4.08 | 11.7 | Ir |
| 1 | 4-F | 3-Br | H | H | | 38.2 | 24 | Is |
| 1 | 5-F | 3-Br | H | H | | <0.1 | 0.2 | It |
| 1 | 6-F | 3-Br | H | H | | 45.5 | 68.7 | Iu |
| 1 | 5-I | 3-CH$_3$ | H | H | | 492.96 | 80.86* | Iak |
| 1 | 7-I | 3-CH$_3$ | H | H | | 28.28 | 323.11 | Ial |
| 1 | 5-F | 3-CH$_3$ | H | COCH$_3$ | | 7.64* | 5.84* | Iam |
| 1 | 5-F | 3-CN | H | H | | <0.1 | <0.1 | Ian |
| 1 | 5-F | 3-CH$_2$OH | H | H | | <0.1 | 0.43 | Iaq |
| 0 | | 3-F | H | H | | 1.58 | 33.41 | |
| 0 | | H | H | C(Y)R$^7$ | CH$_3$ | 60 | 40 | Iv |
| 0 | | 3-CH$_3$ | H | C(Y)R$^7$ | CH$_3$ | 360 | 340 | Iw |
| 0 | | 3-CH$_3$ | H | C(Y)R$^7$ | (CH$_2$)$_4$NH$_2$ | 80 | 70 | Iz |
| 1 | 6-F | 3-CH$_3$ | H | C(Y)R$^7$ | CH$_3$ | 44 | 297 | Iac |
| 1 | 5-F | 3-CH$_3$ | H | C(Y)R$^7$ | (CH$_2$)$_4$NH$_2$ | 40 | 158 | Iad |
| 1 | 6-F | 3-CH$_3$ | H | C(Y)R$^7$ | (CH$_2$)$_4$NH$_2$ | 147.31 | 328.09 | Iae |
| 1 | 5-F | 3-CH$_3$ | H | C(Y)R$^7$ | CH$_3$ | 5.89 | 37.74 | Iaf |
| 2 | 5,6-diF | 3-CH$_3$ | H | C(Y)R$^7$ | CH$_3$ | 33.06 | 216.9 | Iar |
| 2 | 5,6-diF | 3-CH$_3$ | H | C(Y)R$^7$ | (CH$_2$)$_4$NH$_2$ | 30.69 | 301.87 | Ias |

*IC$_{50}$ concentration in μM

What is claimed is:

1. An arylbenzazole compound represented by the structural formula 1 below, or a pharmaceutically acceptable salt thereof,

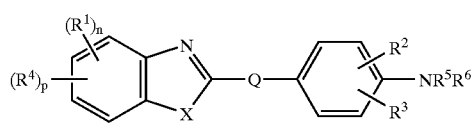

(I)

wherein

X represents S or O;

R$^1$ independently represents fluoro, iodo or trimethyltin;

R$^2$ represents hydrogen, NO$_2$, N$_3$, halogen, alkyl, a halo substituted or hydroxy substituted alkyl, CN or CF$_3$;

R$^3$ represents hydrogen, halogen, alkyl, or a halo substituted or hydroxy substituted alkyl;

R$^4$ independently represents alkyl, a halo substituted or hydroxy substituted alkyl, hydroxyl, alkoxy or aralkoxy;

R$^5$ and R$^6$ each independently represent hydrogen, an amino acid, an alkyl, or a group

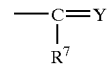

wherein Y represents O or S, and R$^7$ represents alkyl or —CH(R$^8$)NH$_2$ where R$^8$ represents hydrogen, or an optionally substituted alkyl;

Q represents a direct bond, —CH$_2$— or —CH=CH—;

p represents zero, 1 or 2; and n represents zero, 1, 2 or 3; subject to the following provisos:
(a) alkyl or substituted alkyl groups include linear, branched or cyclic structures but when present as linear or branched structures in the compound or as a moiety in another group such as alkoxy they are composed of less then ten carbon atoms;
(b) p represents zero or 1 when n represents 3;
(c) when N represents zero, at least one of R$^5$ or R$^6$ represents —C(Y)—CH(R$^8$)NH$_2$;
(d) when a group is optionally substituted, unless otherwise specified, the substituent is selected from one or more of the following: a halogen, OH, SH, NH$_2$, COOH and CONH$_2$.

2. An arylbenzazole compound of claim 1 with at least one the following features:
(a) alkyl groups when present as such or as a moiety in other groups such as alkoxy each contain less than six carbon atoms;
(b) at least some alkyl groups when present as such or as a moiety in ether groups such as alkoxy are methyl or ethyl; or

29

(c) halogen substitutents, when present, are selected from fluorine, iodine, bromine and chlorine.

3. An arylbenzazole compound of claim 2 where the halogen substituent is fluorine.

4. An arylbenzazole compound of claim 3 wherein said fluorine substituent is the isotope $^{18}$F.

5. An arylbenzazole compound of claim 1 or 2 wherein $R^1$ is fluorine.

6. An arylbenzazole compound of claim 1 wherein $R^1$ is in the 5-position of the benzazole moiety.

7. An arylbenzazole compound of claim 1 wherein $R^2$ is a substitutent in the 3' position of the phenyl group.

8. An arylbenzazole compound of claim 1 wherein X is sulphur.

9. An arylbenzazole compound of claim 1 wherein one of $R^5$ and $R^6$ is C(Y)—CH($R^8$)NH$_2$ or a salt thereof, and the other is hydrogen.

10. An arylbenzazole compound of claim 1 wherein Y is O and $R^8$ is selected from hydrogen, —CH$_3$, —(CH$_2$)$_4$NH$_2$ or —CH$_2$OH.

11. An arylbenzazole compound which is one of the following:

4 Fluoro-2-(4'-amino-3'-methylpheyl)benzothiazole;
6 Fluoro 2-(4'-amino-3'-phenymetylphenyl)benzothiazole;
4 Fluoro-2-(4'-aminophenyl)benzothiazole;
6-Fluoro-2-(4-amino)benzothiazole;
4,5-Difluoro-2-(4'-amino-3'-methylphenyl)benzothiazole;
4,6-Difluoro-2-(4'-amino-3'-methylphenyl)benzothiazole;
5,7-Difluoro-2-(4'-amino-3'-methylphenyl)benzothiazole;
7-Fluoro-2-(4'-amino-3'-methylphenyl)benzothiazole;
5,6-Difluoro-2-(4'-amino-3'-methylphenyl)benzothiazole,
6,7-Difluoro-2-(4'-amino-3'-methylphenyl)benzothiazole;
5-Fluoro-2-(4'-amino-3'-methylphenyl)benzothiazole;
5-Fluoro-2-(4'-aminophenyl)benzothiazole;
4-Fluoro-2-(4'-amino-3'-iodophenyl)benzothiazole;
5-Fluoro-2-(4'-amino-3'-iodophenyl)benzothiazole;
6-Fluoro-2-(4'-amino-3'-iodophenyl)benzothiazole;
4-Fluoro-2-(4'-amino-3'-chlorophenyl)benzothiazole;
5-Fluoro-2-(4'-amino-3'-chlorophenyl)benzothiazole;
6-Fluoro-2-(4'-amino-3'-chlorophenyl)benzothiazole;
4-Fluoro-2-(4'-amino-3'-bromophenyl)benozothiazole;
5-Fluoro-2-(4'-amino-3'-bromophenyl)benozothiazole;
6-Fluoro-2-(4'-amino-3'-bromophenyl)benozothiazole;
2-(4"-Aminophenyl)benzothiazole alanyl amide hydrochloride salt;
2-(4'-Amino-3'-methylphenyl)benzothiazole alanyl amide hydrochloride salt;
2-(4-Amino-3'-chlorophenyl)benzothiazole alanyl amide hydrochloride salt;
2-(4'-Aminophenyl)benzothiazole lysyl amide dihydrochloride salt;
2-(4'-Amino-3'-methylphenyl)benzothiazole lysyl amide dihydrochloride salt;
2-(4'-Amino-3'-chlorophenyl)benzothiazole lysyl amide dihydrochlonide salt;
2-(4'-Amino-3'-methylphenyl)benzothiazole serine hydrochloride salt;
6-Fluoro-2-(4'-amino-3'-methylphenyl)benzothiazole alanyl amide hydrochloride salt;
5-Fluoro-2-(4'-amino-3'methylphenyl)benzothiazole lysyl amide dihydrochloride salt;

30

6-Fluoro-2-(4'-amino-3'-methylphenyl)benzothiazole lysyl amide dihydrochloride salt;
5-Fluoro-2-(4'-amino-3'-methylphenyl)benzothiazole alanyl amide hydrochloride salt;
5-Fluoro-2-(4'-amino-3'-methylphenyl)benzothiazole glycyl amide hydrochloride salt,
5-lodo-2-(4'-amino-3'-methylphenyl)benzothiazole;
7-lodo-2-(4'-amino-3'-methylphenyl)benzothiazole;
5-Fluoro-2-(4'-acetamido-3'-methylphenyl) benzothiazole;
5-Fluoro-2-(4'-amino-3'-cyanophenyl)benzothiazole;
4-Fluoro-2-(4'-amino-3'-cyanophenyl)benzothiazole;
6-Fluoro-2-(4'-amino-3'-cyanophenyl)benzothiazole;
5-Fluoro-2-(4'-amino-3'-(hydroxymethyl)phenyl) benzothiazole;
5,6-Difluoro-2-(4'-amino-3'methylphenyl)benzothiazole alanyl amide hydrochloride salt;
5,6-Difluoro-2-(4'-amino-3'methylphenyl)benzothiazole lysyl amide dihydrochlororide salt; and
5-Trimethylstannyl-2-(4'-amino-3'-methylphenyl) benzothiazole.

12. An arylbenzazole compound of claim 1 for use in therapy as an active therapeutic substance wherein said arylbenzazole compound is an acid addition salt derived from an acid selected from the group consisting of: hydrochloric, hydrobromic, sulphuric, nitric, phosphoric, maleic, salicylic, p-toluenesulphonic, tartaric, citric, lactobionic, formic, malonic, pantothenic, succinic, naphthalene-2-sulphonic, benzenesulphonic, methanesulphonic and ethanesulphonic.

13. A isoropically labelled arylbenzazole compound selected from the group consisting of 5-$^{18}$Fluoro-2-(4'-amino-3'-methylphenyl)benzothiazole and 6-$^{18}$Fluoro-2-(4'-amino-3'-methylphenyl)benzothiazole.

14. A pharmaceutical formulation comprising a compound of claim 1 and a pharmaceuically acceptable carrier.

15. A medical preparation comprising: a therapeutically effective amount of a compound of claim 1 and a pharmaceutically inert excipient.

16. A unit dosage of a pharmaceutical preparation as an antitumour agent in treating mammals comprising a therapeutically-effective non-toxic amount of a compound of claim 1.

17. A method of reducing or inhibiting cancer cell growth in a mammal comprising administering to said mammal an effective amount of an pharmaceutical formulation according to claim 14.

18. An arylbenzazole compound of claim 1 or 2 wherein p=0, $R^5$ and $R^6$ represent a hydrogen atom, $R^3$ represents a hydrogen atom, X represents a sulfur atom, and $R^2$ is selected from 3'-Me, 3'-Et, 3'-Br, 3'-Cl, 3'-CN or 3'-F.

19. An arylbenzazole compound of claim 1 or 2 wherein p=0, $R^5$ and $R^6$ represent a hydrogen atom, $R^3$ represents a hydrogen atom, X represents an oxygen atom, and $R^2$ represents 3'-1.

20. An arylbenzazole compound of claim 1 or 2 wherein p=0, $R^5$ and $R^6$ represent a hydrogen atom, $R^3$ represents 5'-Cl or 5'-Me, X represents an sulfur atom, and $R^2$ represents 3'-Cl.

21. An arylbenzazole compound of claim 1 or 2 wherein p=0, $R^5$ and $R^6$ represent a hydrogen atom, $R^3$ represents 5'-Br, X represents an sulfur atom, and $R^2$ represents 3'-Cl.

22. An arylbenzazole compound of claim 1 or 2 wherein p=0, X represents a sulfur atom, wherein $R^3$, $R^5$ and $R^6$ each represent a hydrogen atom, Q represents a direct bond, n represents 1, $R^1$ represents 4-F, and $R^2$ is selected fom 3-$CH_3$, a hydrogen atom, 3-I, 3-Cl, or 3-Br.

23. An arylbenzazole compound of claim 1 or 2 wherein p=0, X represents a sulfur atom, wherein $R^3$, $R^5$ and $R^6$ each represent a hydrogen atom, Q represents a direct bond, n represents 1, $R^1$ represents 6-F, an $R^2$ is selected from 3-$CH_3$, a hydrogen atom, 3-I, 3-Cl, or 3-Br.

24. An arylbenzazole compound of claim 1 or 2 wherein p=0, X represent a sulfur atom, wherein $R^3$, $R^5$ and $R^6$ each represent a hydrogen atom, Q represents a direct bond, n represents 1, $R^1$ represents 5-F, and $R^2$ is selected from 3-$CH_3$, a hydogen atom, 3-I, 3-Cl, or 3-Br.

25. An arylbenzazole compound of claim 1 or 2 wherein p=0, X represents a sulfur atom, wherein $R^3$, $R^5$ and $R^6$ each represent a hydrogen atom, Q represents a direct bond, n represents 1, $R^1$ represents 7-F, and $R^2$ represents 3-$CH_3$.

26. An arylbenazole compound of claim 1 or 2 wherein p=0, X represents a sulfur atom, wherein $R^3$, $R^5$ and $R^6$ each represent a hydrogen atom, Q represents a direct bond, n represents 2, $R^2$ represents 3-$CH_3$, and $R^1$ represents a 4,5-diF, 4,6-diF, 5–7-diF, or 6,7-diF.

27. An arylbenzazole compound of claim 1 or 2 wherein p=0, X represents S, Q represents a direct bond, one of $R^5$ and $R^6$ represents a hydrogen atom and the other represents —C(O)CH($R^8$)$NH_2$, $R^3$ represents a hydrogen atom, n represents 0, $R^2$ represents a hydrogen atom and $R^8$ represents a group selected from —$CH_3$ or (—$CH_2$)$_4NH_2$.

28. An arylbenzazole compound of claim 1 or 2 wherein p=0, X represents S, Q represents a direct bond, one of $R^5$ and $R^6$ represents a hydrogen atom and the other represents —C(O)CH($R^8$)$NH_2$, $R^3$ represents a hydrogen atom, n represents 0, $R^2$ represents 3-$CH_3$ and $R^8$ represents a group selected from —$CH_3$, —($CH_2$)$_4NH_2$, or $CH_2OH$.

29. An arylbenzazole compound of claim 1 or 2 wherein p=0, X represents S, Q represents a direct bond, one of $R^5$ and $R^6$ represents a hydrogen atom and the other represents —C(O)CH($R^8$)$NH_2$, $R^3$ represents a hydrogen atom, n represents 0, $R^2$ represents 3-Cl and $R^8$ represents a group selected from —$CH_3$ or —($CH_2$)$_4NH_2$.

30. An arylbenzazole compound of claim 1 or 2 wherein p=0, X represents S, Q represents a direct bond, one of $R^5$ and $R^6$ represents a hydrogen atom and the other represents —C(O)CH($R^8$)$NH_2$, $R^3$ represents a hydrogen atom, n represents 1, $R^2$ represents 3-$CH_3$, $R^1$ represents 5-F, and $R^8$ represents a group selected from —$CH_3$, —($CH_2$)$_4NH_2$, o, a hydrogen atom.

31. An arylbenzazole compound of claim 1 or 2 wherein p=0, X represents S, Q represents a direct bond, one of $R^5$ and $R^6$ represents a hydrogen atom and the other represents —C(O)CH($R^8$)$NH_2$, $R^3$ represents a hydrogen atom, n represents 1, $R^2$ represents 3-$CH_3$, $R^1$ represents 6F, and $R^8$ represents a group selected from —$CH_3$, —($CH_2$)$_4NH_2$, or a hydrogen atom.

32. An arylbenzazole compound represented by the structural formula II below, or a phamaceutically acceptable salt thereof

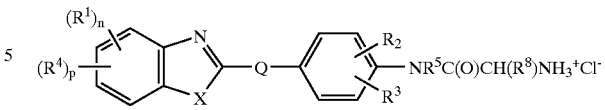
(II)

wherein

X represents S or O;

$R^1$ independently represents fluoro, iodo or trimethyltrin;

$R^2$ represents hydrogen, $NO_2$, $N_3$, halogen, alkyl, a halo substituted or hydroxy substituted alkyl, CN or $CF_3$;

$R^3$ represents hydrogen, halogen, alkyl, or a halo substituted or hydroxy substituted alkyl;

$R^4$ independently represents alkyl, a halo substituted or hydroxy substituted alkyl, hydroxyl, alkoxy or aralkoxy;

$R^5$ represents hydrogen, an amino acid, an alkyl, or a group

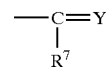

wherein Y represents O or S, and $R^7$ represents alkyl or —CH($R^8$)$NH_2$ where $R^8$ represents hydrogen, or an optionally substituted alkyl;

Q represents a direct bond, —$CH_2$— or —CH=CH—;

p represents zero, 1 or 2; and n represents zero, 1, 2 or 3;

subject to the following provisos:
(a) alkyl or substituted alkyl groups include linear, branched or cyclic structures but when present as linear or branched structures in the compound or as a moiety in another group such as alkoxy they are composed of less then ten carbon atoms;
(b) p represents zero or 1 when n represents 3;
(c) when a group is optionally substituted, unless otherwise specified, the substituent is selected from one or more of the following: a halogen, OH, SH, $NH_2$, COOH and $CONH_2$.

33. A method of preparing the compound of claim 32 comprising reacting a compound of formula III below

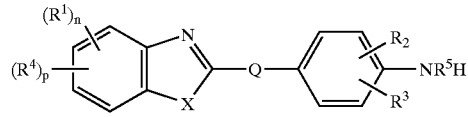
(III)

with a BOC-protected amino acid, followed by hydrochloric acid.

* * * * *

UNITED STATES PATENT AND TRADEMARK OFFICE
CERTIFICATE OF CORRECTION

PATENT NO. : 6,858,633 B1
DATED : February 22, 2005
INVENTOR(S) : Stevens et al.

It is certified that error appears in the above-identified patent and that said Letters Patent is hereby corrected as shown below:

<u>Title page,</u>
Item [30], should read:
-- Foreign Application Priority Data

August 20, 1999   (GB) .................................... 9919673 --.

Signed and Sealed this

Eighth Day of November, 2005

JON W. DUDAS
*Director of the United States Patent and Trademark Office*